(12) United States Patent
Mir

(10) Patent No.: US 9,005,657 B2
(45) Date of Patent: *Apr. 14, 2015

(54) IN SITU MIXING AND APPLICATION OF HYDROCOLLOID SYSTEMS FOR PRE- AND POST HARVEST USE ON AGRICULTURAL CROPS

(71) Applicant: Nazir Mir, Somerset, NJ (US)

(72) Inventor: Nazir Mir, Somerset, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/448,237

(22) Filed: Jul. 31, 2014

(65) Prior Publication Data

US 2014/0342910 A1 Nov. 20, 2014

Related U.S. Application Data

(62) Division of application No. 14/149,990, filed on Jan. 8, 2014, now Pat. No. 8,802,140.

(60) Provisional application No. 61/819,633, filed on May 5, 2013.

(51) Int. Cl.
| | |
|---|---|
| *A61K 9/48* | (2006.01) |
| *A61K 9/14* | (2006.01) |
| *A01N 27/00* | (2006.01) |
| *A61K 31/15* | (2006.01) |
| *A01N 37/44* | (2006.01) |
| *A01N 43/32* | (2006.01) |
| *A01N 43/12* | (2006.01) |

(52) U.S. Cl.
CPC ........... *A01N 27/00* (2013.01); *A01N 37/44* (2013.01); *A01N 43/32* (2013.01); *A01N 43/12* (2013.01)

(58) Field of Classification Search
CPC ........... A61K 9/48; A61K 9/14; A61K 31/15; A01N 27/00
See application file for complete search history.

(56) References Cited

U.S. PATENT DOCUMENTS

| | | | | |
|---|---|---|---|---|
| 7,848,865 | B2 * | 12/2010 | Di Federico et al. | 701/50 |
| 8,163,244 | B2 * | 4/2012 | Yoo | 422/129 |
| 8,377,489 | B2 * | 2/2013 | Edgington et al. | 426/271 |
| 8,802,140 | B2 * | 8/2014 | Mir | 424/451 |
| 2012/0264606 | A1 * | 10/2012 | Kostansek | 504/357 |
| 2013/0065764 | A1 * | 3/2013 | Jacobson et al. | 504/357 |

* cited by examiner

*Primary Examiner* — Alton Pryor
(74) *Attorney, Agent, or Firm* — Law Office of Stephen P. Krupp, PLLC

(57) ABSTRACT

In-situ methods of applying ethylene response manipulation formulations are disclosed. The formulations comprise at least one ethylene response manipulation agent which is at least partially encapsulated, a polyol liquid medium, or a hydrogel medium, or a combination of polyol and hydrogel medium. A preferred ethylene response manipulation agent is 1-methylcyclopropene.

30 Claims, 8 Drawing Sheets

IN SITU MIXING AND APPLICATION OF HYDROCOLLOID SYSTEMS FOR PRE- AND POST HARVEST USE ON AGRICULTURAL CROPS

RELATED APPLICATION

This application is a divisional of and claims priority to U.S. patent application Ser. No. 14/149,990, entitled "In Situ Mixing and Application of Hydrocolloid Systems for Pre- and Post-Harvest Use on Agricultural Crops," filed Jan. 8, 2014, which claims priority to U.S. Provisional Patent Application No. 61/819,633, entitled "In Situ Mixing and Application of Hydrocolloid Systems for Pre- and Post-Harvest Use on Agricultural Crops," filed May 5, 2013, the entire contents of each of which are hereby incorporated by reference. This application is also related to U.S. patent application Ser. No. 13/922,122 filed Jun. 19, 2013.

BACKGROUND OF THE INVENTION

Volatile active compounds such as ethylene response manipulation agents or plant disease and insect controlling materials or other plant growth regulating materials are dispersed in water based mediums and sprayed on crops to improve harvest yield, and subsequent storability of harvested plants and plant parts. These compounds are mostly manufactured in concentrated and generally stable forms by either encapsulation process, or forming salts or conjugated complexes for storage and distribution. The concentrated formulations are then dissolved and diluted to desired application concentrations with water or water based mediums immediately prior to their application on agricultural crops. Once the concentrated compounds are dissolved in water or water based mediums, the volatile active compounds on hydration gets released from the liquid formulation, and are lost to the environment or accumulate in the headspace of the formulation or mixing container, as a result the efficacy of the application solution is reduced. Additionally, under most situations, the complete release of the volatile bioactive compound may take less than 1 hour which makes the biological performance of the liquid application almost ineffective under commercially required spray time of at least 3 to 4 hours. Continued volatile loss from liquid solutions containing bioactive volatile compounds can lead to high vapor pressure buildup in the headspace of mixing tank which can cause explosion and risk workers safety.

U.S. Pat. No. 8,377,489 B2 describes the method of contacting bananas with liquid composition comprising a cyclopropene molecular encapsulation agent complex for a period of 1 to 4 minutes. Since the duration of the liquid contact was small, the authors did not investigate the loss of gaseous 1-MCP from the encapsulated matrix in liquid formulation.

US Patent Application Number 2012/0264606 A1 describes an oil medium for suspending encapsulated MCP particles. The authors then process the suspension in the media mill to produce particles of less than 2 micrometers. When the MCP solution was made from these oil based formulations and then passed through the nozzle of a sprayer, the MCP retention in the spray solution was much better. Authors do not report MCP release kinetics from these oil based formulations. As oils are not miscible with water, producing a homogenous solution to cause consistently a desired effect may be a challenge.

US Patent Application Number 2013/0065764 discloses a formulation which comprises suspended MCP encapsulated materials into non-aqueous organic and synthetic fluids and then bringing the formulation into contact with plant and plant parts. The authors' report that the cyclopropene complex in solution remains in the solid form, minimizing the contact between the cyclopropene compound complex and water, leading to the retention of MCP in the solution for a longer time. The authors do not show any MCP release kinetics data. Moreover, the composition of the disclosed formulations may be inapplicable to ripe or near ripe fruit or plant parts due to the potential for undesirably long residual life of some of the synthetic or organic components of the formulation post application.

The disclosed invention comprises water soluble, environmentally safe and as far as possible, food use approved ingredients that significantly reduce the loss of the volatile active compounds from aqueous solutions leading to sufficient efficacy of liquid formulation or spray solution required to cause a desirable biological effect. The reduction in rapid loss of volatile compounds may help to reduce the volatile accumulation in headspace of mixing tank which can cause potentially explosion hazard in dealing with chemicals of volatile nature. In addition, the invention reduces the resident time of encapsulated volatile 1-MCP compound in the control release 1-MCP liquid formulation from its formation to application onto target plants, thereby, making the spray application more effective, convenient and viable under commercial conditions.

SUMMARY OF THE INVENTION

One aspect of the invention is a method of modifying plant ethylene response comprising the steps of:
a) mixing or suspending 1-methylcyclopropene (1-MCP) at least partially encapsulated with at least one encapsulant, in at least one solvent, to form a 1-MCP control release mixture,
b) forming a 1-MCP control release liquid formulation from the mixture in a continuous stirred tank system, and
c) immediately applying the 1-MCP control release formulation, within or less than 1 hour of formulation formation, onto at least one target plant.

The formulation of the method preferably has a 1-MCP concentration comprising from about 0.01 to about 10,000 milligrams by weight of 1-MCP per liter of formulation. The formulation of the method is preferably applied at a rate of from about 0.1 gram to about 100 grams of 1-MCP per hour.

A second aspect of the invention is a method of modifying plant ethylene response using an automated combination mixing and spraying equipment comprising the steps of:
a) mixing or suspending 1-methylcyclopropene (1-MCP), at least partially encapsulated with at least one encapsulant, in at least one solvent, to form a 1-MCP control release mixture,
b) passing the mixture continuously, or into a stirred tank system, to form a 1-MCP controlled release liquid formulation,
c) applying the volatile 1-MCP control release liquid formulation onto at least one target plant in a time period, wherein the time period is such that the formulation remains sprayable and before the formulation is rendered ineffective to cause an ethylene modifying effect. Preferably, the time period from ethylene modifying formulation formation to its application is 1 hour or lower.

Another aspect of the invention is a postharvest method of modifying plant ethylene response comprising the steps of:

a) mixing or suspending 1-methylcyclopropene (1-MCP) powder encapsulated with at least one encapsulant, in at least one solvent, to form a volatile 1-MCP control release liquid formulation, b) applying the volatile 1-MCP control release liquid formulation onto at least one target plant in a time period, wherein the time period is such that the formulation remains sprayable and before the formulation is rendered ineffective to cause an ethylene modifying effect. Preferably, the time period from ethylene modifying formulation formation to its application is 1 hour or lower.

The encapsulant of any of the methods or aspects of the invention preferably is cyclodextrin; the encapsulant can be α-cyclodextrin or modified α-cyclodextrin; the encapsulant can be β-cyclodextrin or modified β-cyclodextrin; the encapsulant can be γ-cyclodextrin or modified γ-cyclodextrin; or any combination of these α-, β-, and γ-cyclodextrins, and modifications of these isomers, and in any ranges (percentages) of combinations. A preferred combination of these isomers is α-cyclodextrin, modified α-cyclodextrin, modified β-cyclodextrin, and modified γ-cyclodextrin. A preferable proportion of these isomers in combination is from about 50 to about 99.9% α-cyclodextrin, from about 0.1 to about 50% of modified α-cyclodextrin, from about 0.1 to about 50% of modified β-cyclodextrin, and from about 0.1 to about 50% of modified γ-cyclodextrin, all percentages by weight percent of the combination.

Any of the methods or aspects of the invention can have a ratio of encapsulated to non-encapsulated 1-MCP, in any isomeric form or mixture of isomeric forms, including modified or unmodified isomers of cyclodextrin, from about 99:1 to about 50:50.

The formulation of any of the methods or aspect of the invention can further comprise at least one ethylene response manipulation agent which is at least partially encapsulated to form particles, a polyol liquid medium, or a hydrogel medium, or a combination of polyol and hydrogel medium, wherein the particles are dispersed or mixed in said medium, wherein said ethylene response manipulation agent comprises cyclopropene, cyclopropene conjugates, cyclopropene salts or cyclopropene encapsulating materials.

The formulation of any of the methods or aspects of the invention can further comprise at least one colloidal solution selected from the group consisting of mineral oil or other hydrocarbon based oils, paraffin waxes and naturally produced plant lipids.

The formulation of any of the methods (or aspects) of the invention can further comprise at least one anti-microbial, preferably selected from the group consisting of chlorine dioxide, sulphur dioxide, thymol, carvacrol, cinnamaldehyde, allyl isothiocyanate, ethanol, oregano extracts, other synthetic or natural occurring flavanols, phenolic compounds and organic acids.

The formulation of any of the methods or aspects of the invention can further comprise at least one anti-oxidant, preferably wherein the antioxidant is diphenyl amine or ethoxyquin.

The formulation of any of the methods or aspects of the invention can further comprise at least one pesticide, preferably selected from the group consisting of fungicide, insecticide and biopesticide.

The formulation of any of the methods or aspects of the invention can further comprise at least one plant growth regulator, preferably selected from the group consisting of gibberellic acid, etheral and aminoethoxyvinylglycine.

For purposes of this invention, a formulation is rendered ineffective wherein the loss of volatile 1-MCP compound from the liquid formulation exceeds 80% by weight. For example, 100 mL of volatile 1-MCP control release liquid formulation, containing 0.825% of volatile or gaseous 1-MCP is mixed with 100 mL of H2O and then sprayed or applied into 255 L of airtight chamber. The 1-MCP concentration in the headspace of the 255 L chamber is measured once the volatile 1-MCP release from the sprayed formulation is complete and in equilibrium with the head space of the airtight chamber which generally takes place in approximately 4 hours after spraying in the airtight chamber. Gas sample from the headspace of the chamber is withdrawn and 1-MCP is quantified based on the method described by Mir et al. (Nazir A. Mir, Erin Curell, Najma Khan, Melissa Whitaker, and Randolph M. Beaudry. "Harvest maturity, storage temperature and 1-MCP application frequency alter firmness retention and chlorophyll fluorescence of "Redchief Delicious" apples," Journal of American society of horticultural science, 2001, 126(5): 618-624). The formulation is considered ineffective if the volatile or gaseous 1-MCP quantified in the headspace of the chamber is less than 0.165%.

BRIEF DESCRIPTION OF THE FIGURES

FIG. 6 has two components: 6A and 6B.

DETAILED DESCRIPTION OF THE INVENTION

Figure 1:
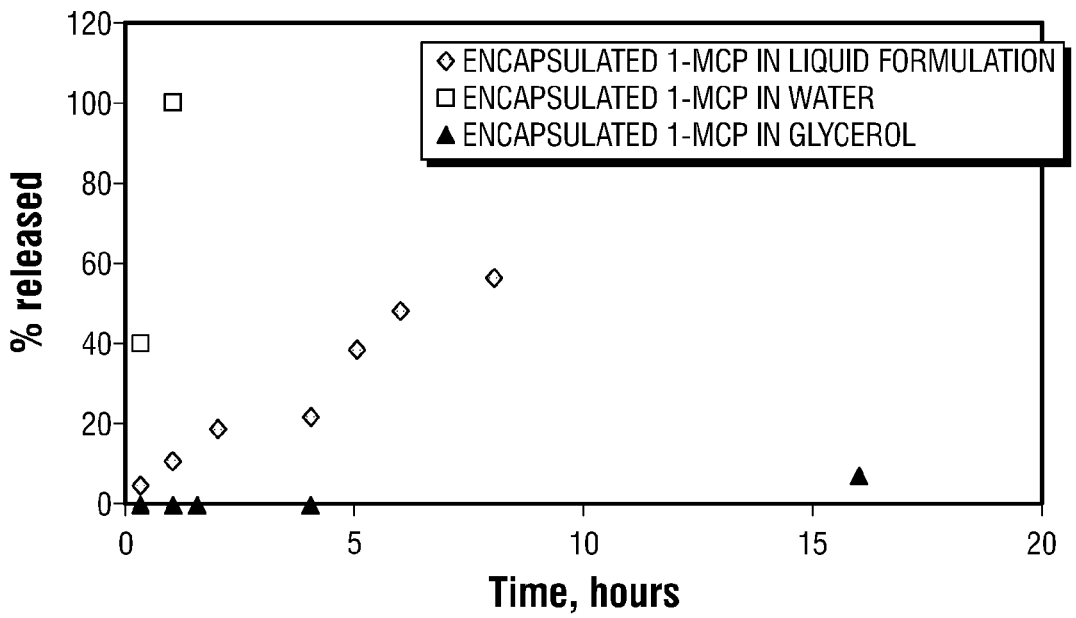
FIG. 1 shows the percentage release of 1-MCP gas from encapsulated 1-MCP dispersed in glycerol, in comparison to water and liquid formulation (Controls). Plotted from Data of Table 1.
Figure 2:
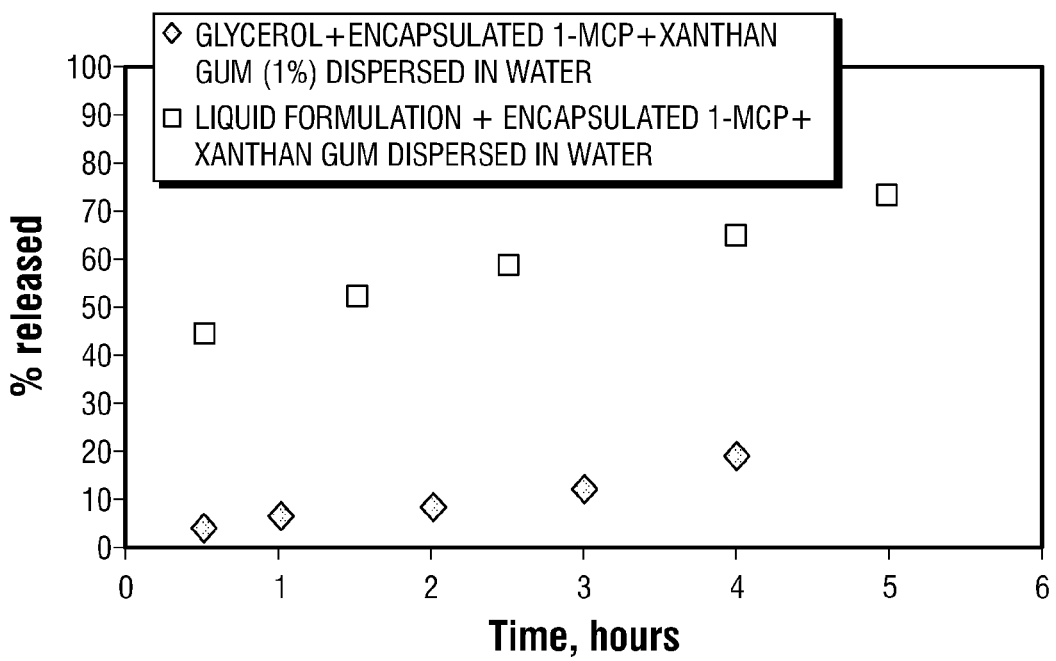
FIG. 2 shows percentage 1-MCP gas released from encapsulated 1-MCP dispersed in glycerol/Xanthan gum system in comparison to liquid formulation/Xanthan gum system (hours). Plotted from Data of Table 2.

Ethylene response manipulation agents include ethylene analogues such as propylene, acetylene, carbon monoxide, 1-butene, etc.; Ethylene releasing compounds such as 2-(chloroethyl)phosphonic acid [commercial name is Etheral], 2-(chloroethylmethyl)bis(phenylmethoxy)silane [commercial name is Silaid], 2-(chloroethyl)tris(2-methoxyethoxy)Silane [commercial name is Alsol]; Ethylene synthesis inhibitors such as aminoethoxyvinylglycine (AVG) [commercial name is RETAIN], aminooxyacetic acid (AOA); and Ethylene action inhibitors such as Silver ions, 2,5-norbornadiene (NBD) and 1-methylcycopropene.

While the invention discloses formulations for encapsulated 1-MCP, a person with ordinary skill and art can use the invention for other control release ethylene manipulation agents as listed above or other chemicals of agricultural importance.

Polyols are used as dispersing agents for cyclodextrin encapsulated 1-methylcyclopropene (1-MCP). Besides cyclodextrin, other encapsulants include those identified in U.S. Patent Application US 2013/0065764 A1, Cucurbit[6]uril byZhang et. al., (Quan Zhang, Zeng Zhen, Hong Jiang, Xue-Gang Li, and Jun-An Liu. "Encapslation of ethylene inhibitor 1-Methylcyclopropene by Cucurbit[6]uril," Journal of Agricultural and Food Chemistry, 2011, 59: 10539-10545) cyclodextrin nanosponges by Trotta et. al. (Francesco Trotta, Roberta Cavalli, Katia Martina, Miriam Biasizzo, Jenny Vitillo, Silvia Bordiga, Pradeep Vavia and Khalid Ansari. "Cyclodextrin nanosponges as effective gas carriers," Journal of inclusión phenomena and microcyclic chemistry, 2011, 71: 189-194) the disclosures of which are incorporated herein by reference. Cyclodextrin (or some isomerized version of cyclodextrin) is preferred encapsulant. Useful polyols for the invention are glycerol (99.9% pure, Sigma Aldrich Co., St. Louis, Mo.) and D-sorbitol (98% pure, Sigma Chemical Co., St. Louis, Mo.). Other polyols that can be used include di, tri, tetrols and other sugar alcohols, and/or mixtures of these.

One preferred formulation 25 mg of encapsulated 1-MCP are dispersed or mixed in 23 mL of glycerol or D-sorbitol. To make the formulation, the contents are stirred well in a 500 mL mason jar to ensure that 1-MCP particles are uniformly dispersed. Different concentrations of hydrocolloid ranging from 0.005% to 1.0% (w/v) are made by hydrating the hydrocolloid by constantly stirring in water. Hydrocolloids include all hydrophilic polymers dispersed in water Selected examples include hydrocolloids such as Xanthan gum (CP Kelko, Atlanta, Ga.), Carboxy Methyl Cellulose (CMC) (CP Kelko, Atlanta, Ga.), carageenan (CP Kelko), hydroxyl propyl cellulose (Fisher Scientific) and Hydroxyethyl cellulose (Fisher Scientific). Xanthan gum is hydrated by slightly heating the solution, along with stifling it constantly. On completion of hydration, 77 mL of the colloidal solution is stirred and mixed to the polyol/1-MCP dispersion to ensure complete mixing and bring the total volume of the solution to 100 mL. The solution is then placed inside an airtight chamber to quantify the amount of 1-MCP released over time.

Controls (Comparative Examples) used to evaluate the benefit of the invention are (a) 25 mg of encapsulated 1-MCP in water; (b) 25 mg of encapsulated 1-MCP in liquid formulation comprising volatile absorption compounds; (c) 25 mg of encapsulated 1-MCP dispersed or mixed in 2 mL of liquid formulation and the volume made up to 100 mL using 1% hydrated Xanthan gum (comparison is carried out by replacing liquid formulation with glycerol). In all cases, the resultant encapsulated 1-MCP dispersed mixture is placed in an airtight chamber to quantify the amount of 1-MCP released over time.

Quantification of volatile or gaseous 1-MCP is done using gas chromatography (GC) based on the method described by Mir et al., (Nazir A. Mir, Erin Curell, Najma Khan, Melissa Whitaker, and Randolph M. Beaudry. "Harvest maturity, storage temperature and 1-MCP application frequency alter firmness retention and chlorophyll fluorescence of "Redchief Delicious" apples," Journal of American society of horticultural science, 2001, 126(5): 618-624). Known volume/amount of the volatile 1-MCP control release liquid formulation is placed inside an airtight chamber of known volume. Gas samples (500 µL) are periodically withdrawn from the head space of the airtight chamber and the percentage release is plotted over time to evaluate efficacy of the invention.

The effectiveness of the volatile 1-MCP control release liquid formulation is evaluated by spraying or applying a known volume of the volatile 1-MCP control release liquid formulation into an airtight chamber of known volume. Gas samples (500 µL) are withdrawn from the head space of the airtight chamber periodically and quantification of volatile or gaseous 1-MCP is done using gas chromatography (GC) based on the method described by Mir et al., (Nazir A. Mir, Erin Curell, Najma Khan, Melissa Whitaker, and Randolph M. Beaudry. "Harvest maturity, storage temperature and 1-MCP application frequency alter firmness retention and chlorophyll fluorescence of "Redchief Delicious" apples," Journal of American society of horticultural science, 2001, 126(5): 618-624). The effectiveness of the volatile 1-MCP control release liquid formulation to cause an ethylene modifying effect is acceptable when 80% by weight or more of gaseous or volatile 1-MCP is released into the headspace of the airtight chamber from the sprayed or applied formulation. If the gaseous or volatile 1-MCP released into the headspace of the airtight chamber from the sprayed or applied volatile 1-MCP control release liquid formulation is less than 80% by weight in comparison to the initial weight of gaseous or volatile 1-MCP in the sprayed or applied volatile 1-MCP control release liquid formulation, then the formulation is rendered ineffective The dispersion and release characteristics of encapsulated 1-MCP are done by (a) using polyols alone, (b) combining hydrocolloid with polyol and (c) dispersing compound in colloidal gels.

Dispersion and containment of 1-MCP in polyols is evaluated using 99.9% pure glycerol and 70% solution of D-sorbitol. 25 mg of encapsulated 1-MCP is dispersed in 1 mL of either glycerol or sorbitol. The mixture is then placed in an airtight chamber to quantify the amount of 1-MCP released over time. Quantification of 1-MCP over time is done with GC as described earlier.

Dispersion and containment of 1-MCP in a combination of hydrocolloid and polyol is evaluated by mixing 25 mg of 1-MCP and 25 mg of Xanthan gum. The solid mixture is then dispersed in 23 mL glycerol. The solution is placed in an airtight chamber to quantify the amount of 1-MCP released over time. Quantification of 1-MCP over time is done with GC as described earlier.

Colloidal gels are made by hydrating hydrocolloids with water as a dispersion medium to form a gel or gel like consistency. Xanthan gum and hydroxyl ethyl cellulose are the two hydrocolloids evaluated for the invention. Three concentrations of Xanthan gum are evaluated for the invention. 0.5%, 0.05% and 0.005% xanthan gum is hydrated with water to form colloidal suspensions in low concentrations to weak gels at high concentrations. 25 mg of 1-MCP is dispersed or mixed in 98 mL Xanthan gum solution and stirred well. The mixture is then placed in an airtight chamber to quantify the amount of 1-MCP released over time. Quantification of 1-MCP over time is done with GC as described earlier. Similar invention is done with hydroxy ethyl cellulose (HEC) where 0.05% of colloidal suspension is made with water. 25 mg of 1-MCP is dispersed in 23 mL colloidal solution of HEC and 77 mL of 0.05% solution of Xanthan gum in water is stirred to the mixture. The mixture is then placed in an airtight chamber to quantify the amount of 1-MCP released over time. Quantification of 1-MCP over time is done with GC as described earlier.

The effect of delivering the preferred solution using spraying over a stagnant system is carried out. 25 mg of encapsulated 1-MCP is dispersed in 23 mL glycerol or D-sorbitol. The contents are stirred well in a 500 mL mason jar to ensure that 1-MCP is uniformly dispersed. 0.05% Xanthan gum is hydrated in water and 77 mL of the colloidal solution is mixed with the above 1-MCP/polyol mixture. The percentage 1-MCP released over time is evaluated by (a) placing the mixture in an airtight chamber (stagnant) (b) spraying the mixture in an airtight chamber.

The ability to entrap 1-MCP in a concentrated polyol blend system was evaluated prior to the addition of the water/Xanthan gum system. The effect of 1-MCP release from the concentrated blend of polyol/hydrocolloid/clay without the addition of hydrated colloidal solution was carried out in a 500 mL jar and the amount of 1-MCP released is quantified using GC for 69 hours. The following formulations were evaluated and all contain 25 mg of encapsulated 1-MCP dispersed in the preferred formulation. The formulations evaluated are (1) 0.5 mg of hydroxyl propyl cellulose (HPC) in 10 mL glycerol; (2) 0.25 g of HPC and 0.25 g of laponite in 10 mL of glycerol; (3) 0.5 g of HPC and 0.5 g of laponite in 10 mL glycerol (4) 0.5 g of hydroxyl propyl cellulose (HPC) in 9 mL glycerol and 1 mL of polysorbate (available from Sigma Aldrich); (5) 0.25 g of HPC and 0.25 g of laponite in 9 mL glycerol and 1 mL polysorbate; (6) 0.5 g of HPC and 0.5 g of laponite in 9 mL glycerol and 1 mL polysorbate.

The release rate of 1-MCP on combining the concentrated polyol blend system with water/Xanthan gum mixture was evaluated by dispersing (a) 0.5 g of hydroxyl propyl cellulose (HPC) in 9 mL of glycerol and 1 mL polysorbate or (b) 0.25 g of HPC and 0.25 g of laponite in 9 mL of glycerol and 1 mL polysorbate or (c) 0.5 g of HPC and 0.5 g of laponite in 9 mL glycerol and 1 mL polysorbate (d) 0.5 g of HPC, 0.5 g of laponite and 0.5 g of tetra sodium pyrophosphate in 9 mL glycerol and 1 mL polysorbate. On dispersion, 25 mg of encapsulated 1-MCP is mixed to either solution (a) or (b) or (c) or (d). To make the formulation, the contents are stirred well in a 500 mL mason jar to ensure that 1-MCP is uniformly dispersed. Xanthan gum (0.05% w/v) is hydrated by heating the solution, along with stifling it constantly. On completion of hydration, 90 mL of the colloidal solution is stirred into the encapsulated 1-MCP dispersed formulation (either formulation (a) or (b) or (c) or (d)). The solution is then placed inside an airtight chamber to quantify the amount of 1-MCP released over time.

Addition of maltodextrin to the concentrated polyol blend system was evaluated for its ability to entrap volatile 1-MCP. The formulation is prepared by dispersing (e) 0.5 g of hydroxyl propyl cellulose (HPC) and 0.5 g of maltodextrin in 9 mL glycerol and 1 mL of polysorbate or (f) 0.25 g of HPC, 0.25 g of laponite and 0.5 g maltodextrin in 9 mL glycerol and 1 mL polysorbate. On dispersion, 25 mg of encapsulated 1-MCP is mixed to either solution (e) or (f). To make the formulation, the contents are stirred well in a 500 mL mason jar to ensure that 1-MCP is uniformly dispersed. Xanthan gum (0.05% w/v) is hydrated by heating the solution, along with stirring it constantly. On completion of hydration, 90 mL of the colloidal solution is stirred into the encapsulated 1-MCP dispersed formulation (either formulation (e) or (f). The solution is then placed inside an airtight chamber to quantify the amount of 1-MCP released over time. In order to understand the release profile of 1-MCP and time taken for more than 70% release, 25 mg of encapsulated 1-MCP is dispersed with 0.25 g of HPC and 0.25 g of maltodextrin in 9 mL glycerol and 1 mL of polysorbate. The resultant polyol blend system containing 1-MCP is then mixed with 90 mL of 0.05% (w/v) hydrated Xanthan gum solution. The solution is then placed inside an airtight chamber to quantify the amount of 1-MCP released over time.

The 1-MCP vapor release profile as a function of increase in loading of encapsulated MCP particles to the disclosed formulation of the invention is also shown. Amount of encapsulated 1-MCP in 0.25 g of HPC and 0.25 g of maltodextrin in 9 mL glycerol and 1 mL of polysorbate, was varied from 25 mg to 300 mg and the release is quantified for 3 hours inside an airtight chamber.

Pectin beads containing encapsulated 1-MCP are made first as oil in water emulsion and then gelling with calcium chloride by cross linking. Pectin slurry is made by continuously stirring 5% low methoxy pectin (CP Kelco) in water. Encapsulated 1-MCP emulsion is made by dispersing 25 mg of the encapsulated material in 1 mL of oil and 0.5 mL polysorbate. The oil emulsion is then dispersed in 15 mL of pectin slurry. The resultant oil in water emulsion is then dropped as droplets through a dropper into 1% calcium chloride solution to make the pectin beads. The beads are then filtered and dried. To test the retention of MCP in the beads, 5 grams of pectin beads were added to 95 mL of water and placed for 3 hours in 255 L air tight chamber. The MCP release in the head space of the airtight chamber was measured and it was found that pectin beads retain a significant amount of MCP in the dried form. A person with ordinary skill and art can further improve the method for holding the encapsulated MCP for direct soil application.

In one embodiment, encapsulated bioactive compound, or bioactive compound salts or conjugates such as 1-MCP are dispersed in at least one of the toxicologically acceptable polyols, such as, for example, glycerol, sorbitol, xylitol, manitol, 1,2-propylene glycol or mixtures of these polyols. The polyol or the mixture of polyols is present in the overall composition for dispersion but prior to final dilution for spray application to plant or plant parts is in an amount of 0.1% by weight or more, preferably 1% or more and in particular 5% by weight or more. In some independent embodiments, the polyol or the mixture of polyols is present in the overall composition for dispersion but prior to final dilution for spray application to plant or plant parts is in an amount of 100% by weight or less, preferably 70% by weight or less and in particular 50% by weight or less.

In another embodiment, encapsulated bioactive compound, or bioactive compound salts or conjugates such as 1-MCP are dispersed in at least one of the toxicologically acceptable polyols, such as, for example, glycerol, sorbitol, xylitol, manitol, 1,2-propylene glycol or mixtures of these polyols. The polyol or the mixture of polyols is present in the overall composition in the diluted spray solution for application to plant or plant parts is in an amount of 0.001% by weight or more, preferably 0.01% or more and in particular 0.05% by weight or more. In some independent embodiments, the polyol or the mixture of polyols is present in the overall final composition for plant or plant part application is in an amount of 10% by weight or less, preferably 5% by weight or less and in particular 2% by weight or less.

In another embodiment, the hydrogel agent according to the invention in addition to encapsulated bioactive compound particles, salts or conjugate formulation comprise of at least one binder or thickener, which is present in the compositions according to the invention in a total amount of 0.001% by weight or more, preferably 0.005% or more and in particular 0.05% by weight or more. In some embodiments, in addition to encapsulated bioactive compound particles comprises at least one binder or thickener, which is present in the compositions according to the invention in a total amount of 10% by weight or less, preferably 5% or less and in particular 2% by weight or less. For example, natural and/or synthetic water-soluble polymers, such as xanthan, alginates, carrageens, agar agar, guar gum, gum Arabic, succinoglycan gum, guar flour, carob seed flour, tragacanth, caraya gum, pectins, derivatized celluloses, such as, for example, carboxy-methylcellulose, hydroxyethylcellulose or methyl-hydroxypropylcellulose, hydrophobically modified celluloses, starch and starch ethers are used. Water-soluble carboxyvinyl polymers (e.g. Carbopol grades), polyvinyl alcohol, polyvinylpyrrolidone and higher molecular weight polyethylene glycols (in particular those with molecular weights of 102-106-D) are also suitable for the purpose of the invention. Sheet silicates and finely divided silicas (aerogel silicas and fumed silicas) can likewise be suitable for this application.

Furthermore, gel silcas, xerogel silcas, particulate organic polymers such as polymethacrylate, polyethylene, polypropylene or clay minerals that absorb gasses such as Zeolites or Laponite may be added to the formulation to enhance its efficacy for specific applications. Accordingly, anionic, cationic, nonionic, zwitterionic and ampholytic surfactants with good foam effect may be used to stabilize the formulation and improve application canopy coverage. Oils, fats and wax components can have a complimentary effect on the performance of the application.

In another embodiment, encapsulated bioactive compound, or bioactive compound salts or conjugates such as 1-MCP present in the overall composition of the formulation is in an amount of 0.001% by active ingredient (a.i.) weight or more, preferably 0.005% by a.i. weight or more and in particular 0.05% by a.i. weight or more. In some independent embodiments, encapsulated bioactive compound, or bioactive compound salts or conjugates such as 1-MCP present in the overall composition of the formulation is in an amount of 10% by a.i. weight or less, preferably 5% by a.i. weight or less and in particular 3% by a.i. weight or less.

Bioassay studies are carried out by spraying the preferred solution on tomatoes and the extension in shelf life is recorded. Bioassay of the formulation was performed by spraying the formulation as described above on ripening tomato fruit when they were approximately 50% green, 50% red and held at 22° C. for shelf life evaluation. Compared to the control fruit, where formulation liquid was not sprayed, an extension of 5 days shelf life was observed on fruits sprayed with the formulation. The control fruit had a shelf life of 7 days, while the fruit treated with formulation had a shelf life of 12 days at 22° C.

A related embodiment of the invention is the encapsulation of volatile antimicrobial compounds, where the volatility may vary with temperature, and dispersing the antimicrobial encapsulated material in the polyol or hydrogel or polyol/hydrogel system. The volatile antimicrobials may include chlorine dioxide, sulphur dioxide, thymol, carvacrol, cinnamaldehyde, allyl isothiocyanate, ethanol, oregano extracts and other synthetic or natural occurring flavanols, phenolic compounds or organic acids. The proportion of antimicrobials present in the overall composition of the formulation is in an amount of 0.1 parts per million (ppm, w/v) % or more, preferably 1.0 ppm or more and in particular 10 ppm or more. In some independent embodiments, the amount of antimicrobial compound present in the overall composition of the formulation, is in an amount of 1000 ppm or less, preferably 500 ppm or less and in particular 100 ppm or less.

The encapsulated compounds (or antimicrobial compounds) dispersed in the polyols may be applied alone, in mixtures with each other, or in combination with other ethylene response manipulation agents for pre and post harvest application on plants and plant parts. Post harvest application may include drenching or dipping plants and plant parts in the formulation for time periods generally for less than 1 hour. The harvested plant parts such as fruits, vegetables and flowers can also be sprayed with the 1-MCP control release formulation prior to storage, packing, transit or retail to extend their post-harvest life.

In some embodiments, the proportion of encapsulated 1-MCP to antimicrobial compound present in the formulation is 1:1 or more, preferably 1:100 or more, more preferable 1:1000 or more. In some embodiments, the proportion of encapsulated 1-MCP to antimicrobial compound present in the formulation is 10000:1 or less, preferably 1000:1 or less, more preferable 100:1 or less, either together in the formulation or individually to help maintain quality, prolong shelf life or both. The application of these compounds can be done directly in the field to prevent microbial growth on bruised or cut tissues or post-harvest to prevent spoilage and maintain quality of the food product. The formulation with encapsulated antimicrobial can also be used to help maintain quality and safety of meat, poultry, sea foods, ready to eat meals and other perishable food products, wherein the longevity of the antimicrobials and their activity in the food material would help prevent microbial growth and extend the life of the food product.

In another embodiment, the preferred formulation comprising polyols, or hydrogel, or polyol/hydrogel system, may also contain at least one antioxidant, such as diphenyl amine or ethoxyquin, etc., in addition to encapsulated ethylene response manipulation agents such as 1-MCP for post-harvest application of perishable food products. The antioxidant(s) will help to prevent development of storage disorders of perishable foods such as apple and pear, while as ethylene response manipulation agents will slow ripening and therefore the combined system will deliver an improved quality product at the end of the storage. In this case harvested plant parts such as fruits, vegetables and flowers may generally be drenched or dipped in the 1-MCP control release ethylene response modifying formulation, generally for period of less than 1 hour. The 1-MCP control release ethylene response modifying formulation may also contain the above mentioned antioxidants or other additives to control storage disorders such as superficial scald in apple and pear.

In another embodiment, the preferred formulation comprising polyols, or hydrogel, or polyol/hydrogel system, may contain at least one fungicide, insecticide or biopesticide, plant growth regulators such as Gibberellic Acid (GA3), Etheral, aminoethoxyvinylglycine (AVG), etc. or mixtures of these in addition to encapsulated ethylene response manipulation agents such as 1-MCP for pre harvest application of food crops such as fruit, vegetable and field crops. In this latter embodiment, the ethylene response manipulation agent may help scheduling harvests and improving post-harvest life of the crop, while as the fungicides and insecticides will help to control the insects and diseases on the crops. One obvious benefit of this would be to save on cost that is incurred on individual application of these chemicals. In some embodiments, the proportion of encapsulated 1-MCP to pesticide (fungicides, insecticides, bio pesticides, plant growth regulators, etc.) compound present in the formulation is 1:1 or more, preferably 1:100 or more, more preferable 1:1000 or more. In some embodiments, the proportion of encapsulated 1-MCP to pesticide compound present in the formulation is 1000:1 or less, preferably 1000:1 or less, more preferable 100:1 or less.

In another embodiment such formulations may be used on harvested plant parts. In this case harvested plant parts such as fruits and vegetables may generally be drenched or dipped in the ethylene response modifying formulation which may contain at least one fungicide, insecticide or biopesticide, plant growth regulators such as Gibberellic Acid (GA3), Etheral, aminoethoxyvinylglycine (AVG), etc. or mixtures of these in addition to encapsulated ethylene response manipulation agents such as 1-MCP for post harvest application of food crops such as fruit, vegetables and flowers. In another embodiment, the preferred formulation comprising of polyol or hydrogel or polyol/hydrogel system may contain partially encapsulated ethylene response manipulation agents such as 1-MCP for pre or post-harvest application of perishable food crops. The proportion of the partially encapsulated material such as 1-MCP present in the overall composition of the formulation is in an amount of 1% by weight or more, preferably 5% by weight or more and in particular 10% by weight or more, and can be as much as 100%. In some independent embodiments, the partially encapsulated bioactive compound, or bioactive compound salts or conjugates such as 1-MCP present in the overall composition of the formulation, is in an amount of 90% by weight or less, preferably 70% by weight or less and in particular 50% by weight or less.

So, the 1-MCP may be present in an amount of 100 mg/L but only be 30% of that 1-MCP may be encapsulated (30 mg/L); the remaining 70% (70 mg/L) would be "free" 1-MCP (unencapsulated). Some embodiments may have only 10 mg/L 1-MCP of which 90% (9 mg/L) may be completely encapsulated and remaining 10% 1-MCP (1 mg/L) may be in the free form. Likewise some embodiments may have 10,000 mg/L 1-MCP of which 50% (5000 mg/L) is encapsulated and 50% (500 mg/L exists in non-capsulated forms. Depending on the application, the ratio of encapsulated 1-MCP:non-encapsulated 1-MCP can be from about 99:1 to about 50:50, preferably from about 99:1 to about 75:25. Other scenarios of combining encapsulated and non-encapsulated forms of bioactive compounds such as 1-MCP can be formulated by a person with ordinary skills in the art but without deviating from the scope of this invention.

When more than one bioactive compounds such as 1-MCP or other ethylene response manipulation agents and pesticides such as fungicides, insecticides or other plant growth regulators such as Gibberellic Acid (GA3), Etheral, aminoethoxyvinylglycine (AVG), etc. are dispersed in the disclosed formulation to control ripening, modify plant growth and development or to control diseases of plants or plant parts, 1-MCP can be in either encapsulated or non-encapsulated, or combination of both forms, to yield a desired effect of controlling ripening of plant or plant parts. When a mixture of 1-MCP is present in partially encapsulated and partially non-encapsulated form, the proportion of encapsulated to non-encapsulated 1-MCP can be in the ratio of 100:0, or 70:1 or lower or 50:50 or lower. In some embodiments the proportion of encapsulated to non-encapsulated 1-MCP can be in the ratio of 0:100, or 1:70 or higher or 50:50 or higher. So 1-MCP may be present in an amount of 100 mg/L but only 30% of that 1-MCP may be encapsulated (30 mg/L), the remaining 70% (70 mg/L) would be "free" 1-MCP (non-encapsulated). Some embodiments may have only 10 mg/L 1-MCP of which 90% (9 mg/L) may be completely encapsulated and remaining 10% 1-MCP (1 mg/L) may be in the free form. Likewise some embodiments may have 10,000 mg/L 1-MCP of which 50% (5000 mg/L) is encapsulated and 50% (500 mg/L exists in non-encapsulated forms. Other scenarios of combining encapsulated and non-encapsulated forms of bioactive compounds such as 1-MCP can be formulated by a person with ordinary skills in the art but without deviating from the scope of this invention. In a preferred embodiment shown in FIG. 15, a flash mixing equipment 100 is a modified sprayer, wherein the encapsulated powder containing volatile actives is flash mixed (continuously) with liquid, including but not limited to water, and sprayed on the plant and plant materials almost continuously, so that the volatile materials do not stay longer in the liquid and get lost during the mixing or spraying process. In one aspect of the invention, the resident time of the volatile 1-MCP control release ethylene response modifying formulation may be 1 second or more, preferably 30 seconds or more, more preferably, 60 seconds or more. In one aspect of the invention, the resident time of the volatile 1-MCP control release ethylene response modifying formulation may be 1 hour or less, more preferably, 0.75 hours or less, more preferably, 0.5 hours or less. Most flash mixing equipment are designed to agitate a small amount of non-volatile additive into a continuous stream in such a way that the residence time of the material before it is applied or sprayed to the plants is extremely short and in most cases usually less than 10 minutes. Examples of flash mixing mixers and/or equipment include those manufactured by SILVERSON and MILTON ROY. Thus it is understood that the equipment 100 limits the time of mixing the encapsulated volatiles with liquid material that could break or dissolve encapsulation, and thereby minimize, reduce or stop loss of the volatile actives during mixing and spraying. In the current embodiment, the flash mixing and spraying equipment 100, has a feed tank 101, wherein the water or a colloidal solution is stored. The water/colloidal solution is metered, using the metering valve, 112, to get the right amount into the flash mixing tank 103. At the same time, the encapsulated material is fed through hopper 102 and metered into the flash mixing tank 103, through a metering valve 112. Flash mixing of the volatile actives encapsulated powder with the water/colloidal liquid is done through centrifugal mixing as shown in 104. The mixing and the mixer would ensure quick mixing without breaking the encapsulation in a shortest time possible. The mixing can also be done through a gush of air bubbles by passing pressurized air through the blend in the flash mixer to ensure minimal disruption to encapsulation. The mixed content are further metered through a metering valve into a stirrer unit 114. The stirrer unit 114 is optional and is needed if any other liquid aide or solid aide is used. The liquid/solid aide is metered through the chamber 105 through valve 112 into the stifling chamber 108. The blended liquid/encapsulated powder mixture is stirred with the liquid/solid aide using automated stirrer 106. The excess pressure is vented through pressure release vent 107. The final mixed liquid is metered through a dual valve 115 and pumped through spray pump 110 into the sprayer 111. If the blended material in chamber 108 is unused, it can be discharged through the dual valve 115, into the discharge tube 109. The set-up 100 can be automated with a control panel, wherein the inputs and amounts of materials can be automated and controlled by the operator.

Figure 16:
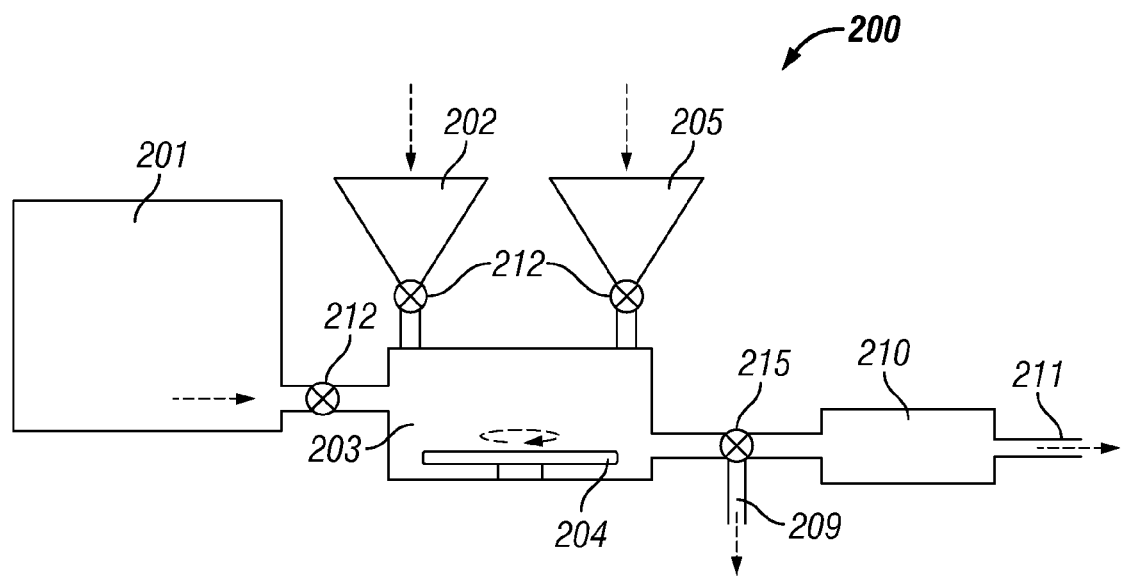
FIG. 16 shows another version of flash mixing equipment used in combination with a modified sprayer of the invention.

In a preferred embodiment shown in FIG. 16, a flash mixing equipment 200 is a modified sprayer, wherein the encapsulated powder containing volatile actives is flash mixed with liquid, including but not limited to water, and sprayed on the plant and plant materials, so that the volatile materials do not stay longer in the liquid and get lost during the mixing or spraying process. Thus it is understood that the equipment 200 limits the time of mixing the encapsulated volatiles with liquid material that could break or dissolve encapsulation, and thereby minimize, reduce or stop loss of the volatile actives during mixing and spraying. In the current embodiment, the flash mixing and spraying equipment 200, has a feed tank 201, wherein the water or a colloidal solution is stored. The water/colloidal solution is metered, using the metering valve 212 to get the right amount into the flash mixing tank 203. At the same time, the encapsulated material is fed through hopper 202 and metered into the flash mixing tank 203, through a metering valve 212; the liquid/solid aide is metered through the hopper 205 and metered into the flash mixing tank 203, through a metering valve 212. Flash mixing of the volatile actives encapsulated powder with the water/colloidal liquid and liquid/solid aides is done through centrifugal mixing as shown in 204. The mixing and the mixer would ensure quick mixing without breaking the encapsulation in a shortest time possible. The mixing can also be done through a gush of air bubbles by passing pressurized air through the blend in the flash mixer to ensure minimal disruption to encapsulation. The final mixed content is further metered through a dual valve 215 and pumped through spray pump 210 into the sprayer 211. If the blended material in flash mixing tank 203 is unused, it can be discharged through the dual valve 215, into the discharge tube 209. The set-up 200 can be automated with a control panel, wherein the inputs and amounts of materials can be automated and controlled by the operator.

Figure 15:
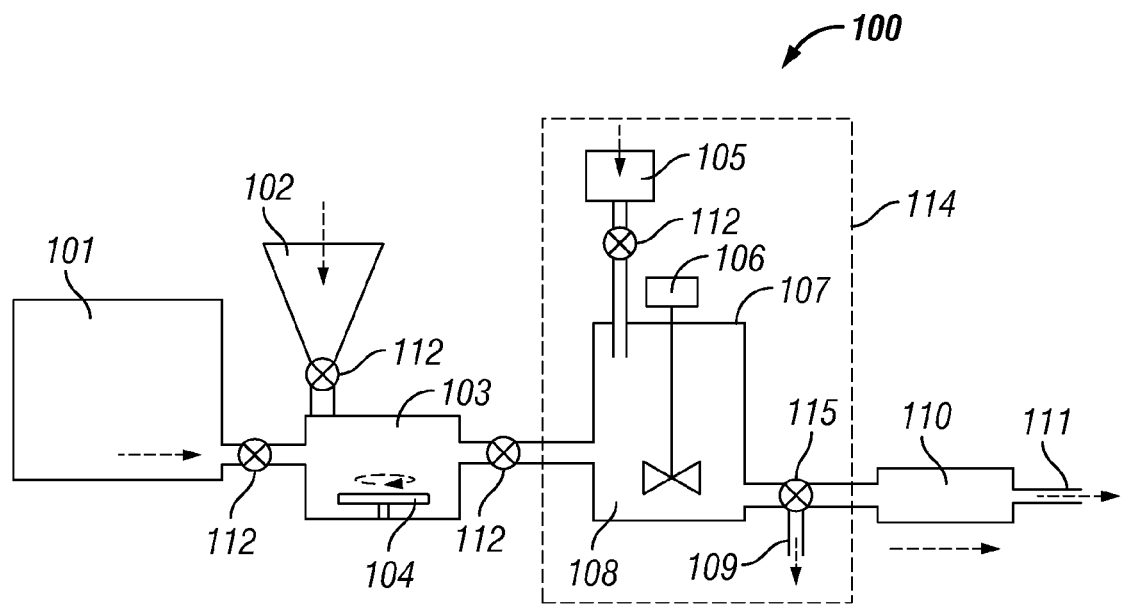
FIG. 15 shows flash mixing equipment used in combination with a modified sprayer of the invention.

The set-up described in FIGS. 15 and 16 can be developed or constructed as a backpack sprayer or a vehicle mounted sprayer as needed for the application.

Table 1 demonstrates that 1-MCP gas is released rapidly when encapsulated 1-MCP powder is dissolved in water (reference). The 100% 1-MCP gas release is complete in 1 hour. By comparison, the 1-MCP gas release from liquid formulation of the example is dramatically reduced. It takes approximately 8 hours to release 57.36% of 1-MCP from the liquid formulation, thereby, allowing the liquid formulation to be biologically effective for longer time compared to the reference. When the encapsulated 1-MCP powder was dispersed in glycerol, the release rate of 1-MCP gas from encapsulated powder is drastically reduced, allowing only 7.53% to be released over a 16 hour holding period at Room Temperature of 22° C.

TABLE 2

Percentage 1-MCP gas released from encapsulated 1-MCP dispersed in glycerol/Xanthan gum system in comparison to liquid formulation/Xanthan gum system

| Glycerol + encapsulated 1-MCP + Xanthan gum (1%) dispersed in water | | liquid formulation + encapsulated 1-MCP + Xanthan gum dispersed in water | | |
|---|---|---|---|---|
| *100% release of 1-MCP from formulation: 1.45 ppm | | | | |
| Time (hours) | ppm | % released | Time (hours) | ppm | % released |
| 0.5 | 0.075 | 5.18 | 0.5 | 0.649 | 44.76 |
| 1 | 0.104 | 7.16 | 1.5 | 0.758 | 52.28 |
| 2 | 0.142 | 9.77 | 2.5 | 0.857 | 59.09 |
| 3 | 0.191 | 13.20 | 4 | 0.944 | 65.09 |
| 4 | 0.295 | 20.37 | 5 | 1.060 | 73.13 |

Table 2 shows that hydrated 1% Xanthan gum in 4 hours releases 20.37% of 1-MCP dispersed in glycerol in comparison to 65.09% released from 1-MCP dispersed in liquid formulation.

TABLE 1

Percentage release of 1-MCP gas from encapsulated 1-MCP dispersed in glycerol, in comparison to water and liquid formulation (Controls)

| encapsulated 1-MCP in liquid formulation | | | encapsulated 1-MCP in water | | | encapsulated 1-MCP in Glycerol | | |
|---|---|---|---|---|---|---|---|---|
| *100% release of 1-MCP from formulation: 1.45 ppm | | | | | | | | |
| Time (hr) | ppm | % released | Time (hr) | ppm | % released | Time (hr) | ppm | % released |
| 0.25 | 0.074 | 5.13 | 0.25 | 0.586 | 40.42 | 0.25 | 0.000 | 0.00 |
| 1 | 0.157 | 10.92 | 1 | 1.452 | 100.12 | 1 | 0.000 | 0.00 |
| 2 | 0.272 | 18.84 | | | | 1.5 | 0.000 | 0.00 |
| 4 | 0.325 | 22.57 | | | | 4 | 0.000 | 0.00 |
| 5 | 0.569 | 39.45 | | | | 16 | 0.109 | 7.53 |
| 6 | 0.694 | 48.12 | | | | | | |
| 8 | 0.827 | 57.36 | | | | | | |

*Verified by releasing 100% 1-MCP with addition of water in 255.5 L air tight chamber

TABLE 3

Effect of varying Xanthan gum concentration on the release of 1-MCP gas from
encapsulated 1-MCP dispersed in D-sorbitol (70%)
Sorbitol (70%) + encapsulated 1-MCP + Xanthan gum dispersed in water
100% release of 1-MCP from formulation: 1.45 ppm

| | 1% XG | | 0.5% XG | | 0.1% XG | | 0.05% XG | | 0.005% XG | | 0% XG | |
|---|---|---|---|---|---|---|---|---|---|---|---|---|
| Time (min) | ppm | % released | ppm | % released | ppm | % released | ppm | % released | ppm | % released | Ppm | % released |
| 0 | 0 | 0.00 | 0 | 0.00 | 0.000 | 0.00 | 0.000 | 0.00 | 0.000 | 0.00 | 0.282 | 19.45 |
| 15 | 0 | 0.00 | 0 | 0.00 | 0.000 | 0.00 | 0.000 | 0.00 | 0.037 | 2.54 | 0.705 | 48.62 |
| 30 | 0 | 0.00 | 0 | 0.00 | 0.021 | 1.46 | 0.014 | 0.95 | 0.123 | 8.51 | 0.974 | 67.17 |
| 45 | 0 | 0.00 | 0 | 0.00 | 0.032 | 2.19 | 0.019 | 1.30 | 0.214 | 14.77 | 1.352 | 93.24 |
| 60 | 0 | 0.00 | 0 | 0.00 | 0.054 | 3.74 | 0.046 | 3.15 | 0.337 | 23.24 | 1.459 | 100.62 |

Different concentrations of Xanthan gum dispersed in water, ranging from 0.005% to 1% is evaluated for their efficacy in controlling release of encapsulated 1-MCP dispersed in D-sorbitol and also compared to the effect of water alone (0% XG in Table 3) in controlling release of encapsulated 1-MCP dispersed in D-sorbitol. The results in Table 3 demonstrate that increasing Xanthan gum concentration in water from 0.005 to 1% slows down the release of encapsulated 1-MCP dispersed in D-sorbitol from 23.24% to 0% in 1 hour. Also replacing Xanthan gum with 100% water (0% XG in Table 3) results in 100% release of encapsulated 1-MCP in 1 hour.

TABLE 4

Effect of varying Xanthan gum concentration on the release of 1-MCP gas
from encapsulated 1-MCP dispersed in Glycerol (99.9%)
Glycerol (99.9%) + encapsulated 1-MCP + Xanthan gum dispersed in water
100% release of 1-MCP from formulation: 1.45 ppm

| | 1% XG | | 0.5% XG | | 0.1% XG | | 0.05% XG | | 0.005% XG | | 0% XG | |
|---|---|---|---|---|---|---|---|---|---|---|---|---|
| Time (min) | ppm | % released | ppm | % released | ppm | % released | ppm | % released | ppm | % released | ppm | % released |
| 0 | 0 | 0.00 | 0 | 0.00 | 0.000 | 0.00 | 0.000 | 0.00 | 0.000 | 0.00 | 0.356 | 24.55 |
| 15 | 0 | 0.00 | 0 | 0.00 | 0.000 | 0.00 | 0.000 | 0.00 | 0.051 | 3.48 | 0.763 | 52.62 |
| 30 | 0 | 0.00 | 0 | 0.00 | 0.000 | 0.00 | 0.000 | 0.00 | 0.103 | 7.07 | 1.035 | 71.34 |
| 45 | 0 | 0.00 | 0 | 0.00 | 0.047 | 3.21 | 0.006 | 0.41 | 0.108 | 7.48 | 1.455 | 100.34 |
| 60 | 0 | 0.00 | 0 | 0.00 | 0.049 | 3.40 | 0.032 | 2.21 | 0.386 | 26.64 | 1.455 | 100.34 |

Different concentrations of Xanthan gum dispersed in water, ranging from 0.005% to 1% is evaluated for their efficacy in controlling release of encapsulated 1-MCP dispersed in Glycerol and also compared to the effect of water alone (0% XG in Table 4) in controlling release of encapsulated 1-MCP dispersed in Glycerol. The results in Table 4 demonstrate that increasing Xanthan gum concentration in water from 0.005 to 1% slows down the release of encapsulated 1-MCP dispersed in Glycerol from 26.64% to 0% in 1 hour. Also replacing Xanthan gum with 100% water (0% XG in Table 3) results in 100% release of encapsulated 1-MCP in 1 hour.

TABLE 5

Release profile of 1-MCP gas from encapsulated 1-MCP
dispersed in sorbitol and in combination with hydrated Xanthan gum
Sorbitol + encapsulated 1-MCP +
Xanthan gum (0.025%) dispersed in water
100% release of 1-MCP from formulation: 1.45 ppm

| Time (hr) | ppm | % released |
|---|---|---|
| 0 | 0.000 | 0.00 |
| 0.25 | 0.000 | 0.00 |
| 0.5 | 0.037 | 2.53 |
| 0.75 | 0.078 | 5.40 |
| 1 | 0.130 | 8.94 |
| 1.25 | 0.113 | 7.79 |
| 1.5 | 0.221 | 15.21 |
| 2.25 | 0.357 | 24.61 |

TABLE 5-continued

Release profile of 1-MCP gas from encapsulated 1-MCP
dispersed in sorbitol and in combination with hydrated Xanthan gum
Sorbitol + encapsulated 1-MCP +
Xanthan gum (0.025%) dispersed in water
100% release of 1-MCP from formulation: 1.45 ppm

| Time (hr) | ppm | % released |
|---|---|---|
| 3 | 0.465 | 32.05 |
| 19 | 0.973 | 67.14 |

Figure 5:
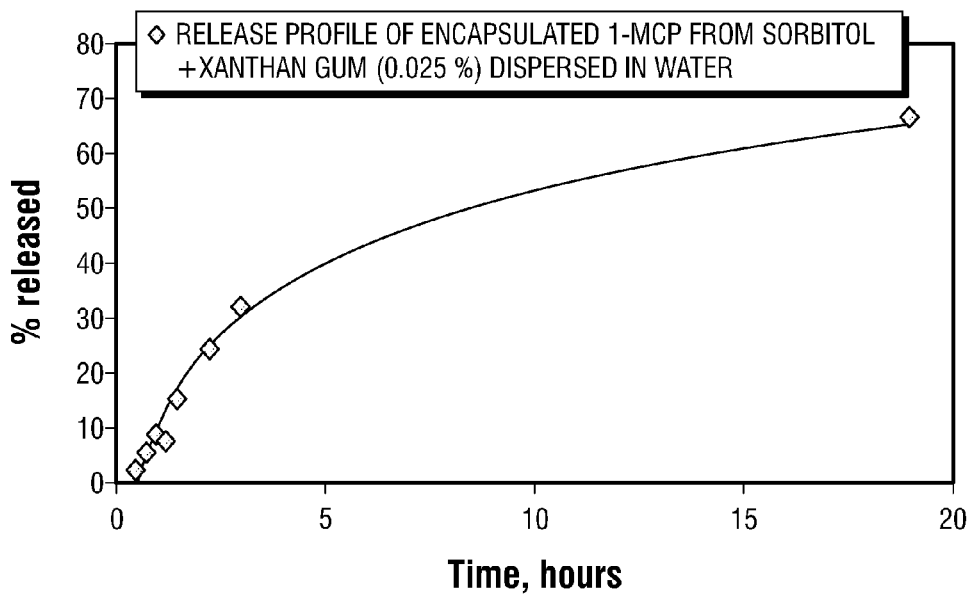
FIG. 5 shows the release profile of 1-MCP gas from encapsulated 1-MCP dispersed in sorbitol and in combination with hydrated Xanthan gum (hours). Plotted from Data of Table 5.

Table 5 and FIG. 5 demonstrate that using hydrated Xanthan gum results in controlled release of encapsulated 1-MCP dispersed in D-sorbitol. About 67% of 1-MCP is released at the end of 19 hours.

TABLE 6

Percentage release of 1-MCP gas when sprayed vs. stagnant from encapsulated 1-MCP dispersed in Glycerol/Xanthan gum/Water or Sorbitol/Xanthan gum/Water system

| Sorbitol + encapsulated 1-MCP + Xanthan gum (0.05%) dispersed in water | | | | Glycerol + encapsulated 1-MCP + Xanthan gum (0.05%) dispersed in water | | | | | | | |
|---|---|---|---|---|---|---|---|---|---|---|---|
| Stagnant | | | Spray | | | Stagnant | | | Spray | | |
| Time (hr) | ppm | % released | Time (hr) | ppm | % released | Time (hr) | ppm | % released | Time (hr) | ppm | % released |
| 0 | 0.000 | 0.00 | 10 | 0.166 | 11.45 | 30 | 0.000 | 0.00 | 0 | 0.000 | 0.00 |
| 15 | 0.000 | 0.00 | 40 | 0.264 | 18.18 | 60 | 0.030 | 2.07 | 15 | 0.044 | 3.02 |
| 30 | 0.028 | 1.91 | 60 | 0.300 | 20.71 | | | | 30 | 0.081 | 5.56 |
| 45 | 0.038 | 2.59 | | | | | | | 45 | 0.126 | 8.66 |
| 60 | 0.091 | 6.29 | | | | | | | 60 | 0.136 | 9.40 |

Figure 6A:
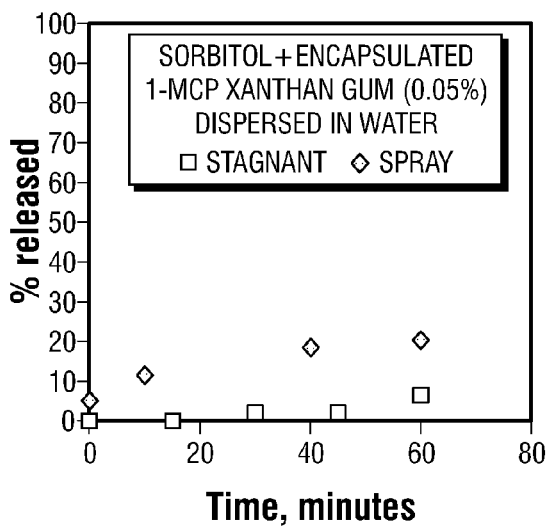
FIG. 6A shows percentage release of 1-MCP gas when sprayed vs. Sorbitol/Xanthan gum/Water system. Plotted from Data of Table 6.
Figure 6B:
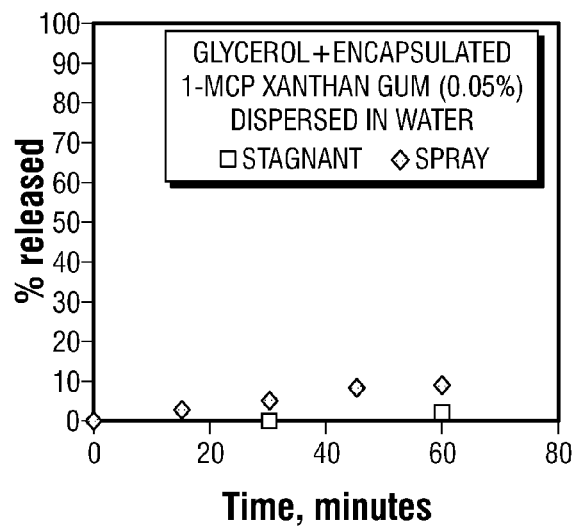
FIG. 6B shows the percentage release of 1-MCP gas when sprayed vs. stagnant from encapsulated 1-MCP dispersed in Glycerol/Xanthan gum/Water.
Figure 7:
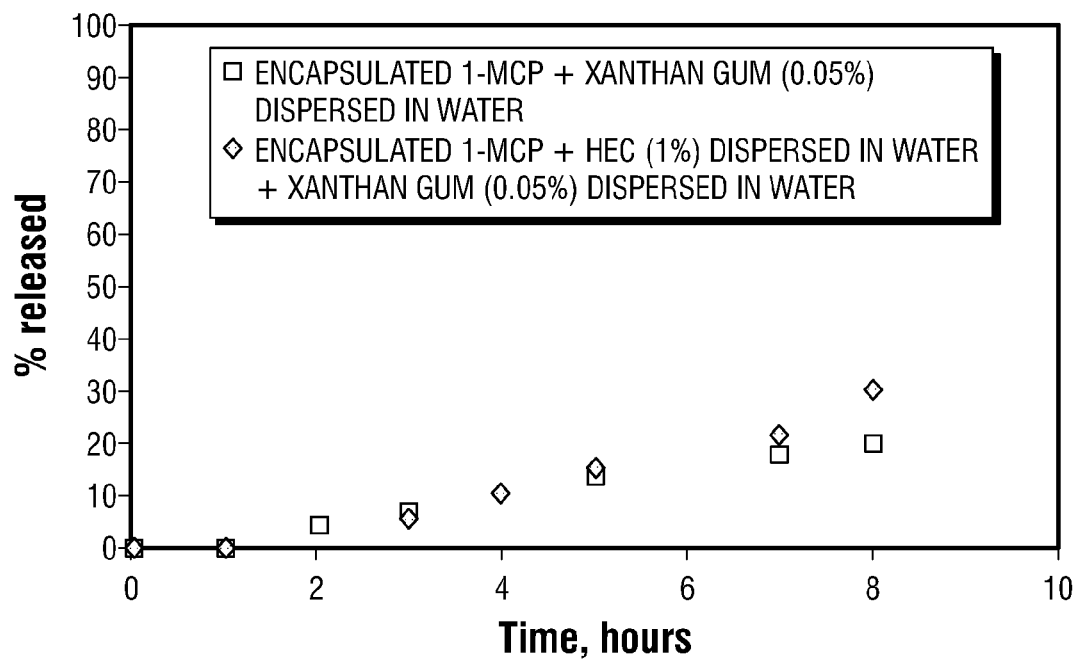
FIG. 7 shows the effect of dispersing encapsulated 1-MCP hydrated Xanthan gum or hydrated Xanthan gum/hydroxyethyl cellulose on its release. Plotted from Data of Table 7.
Figure 8:
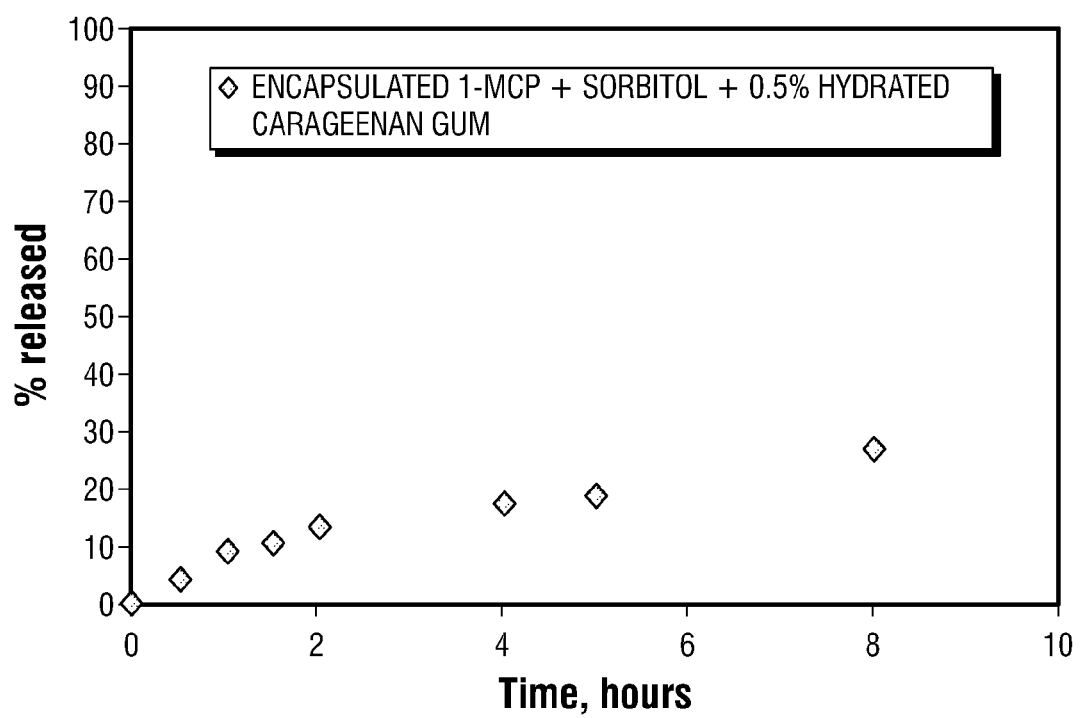
FIG. 8 shows the percentage 1-MCP release from encapsulated 1-MCP dispersed in D-sorbitol mixed with 0.5% hydrated carageenan gum. Plotted from Data of Table 8.
Figure 9:
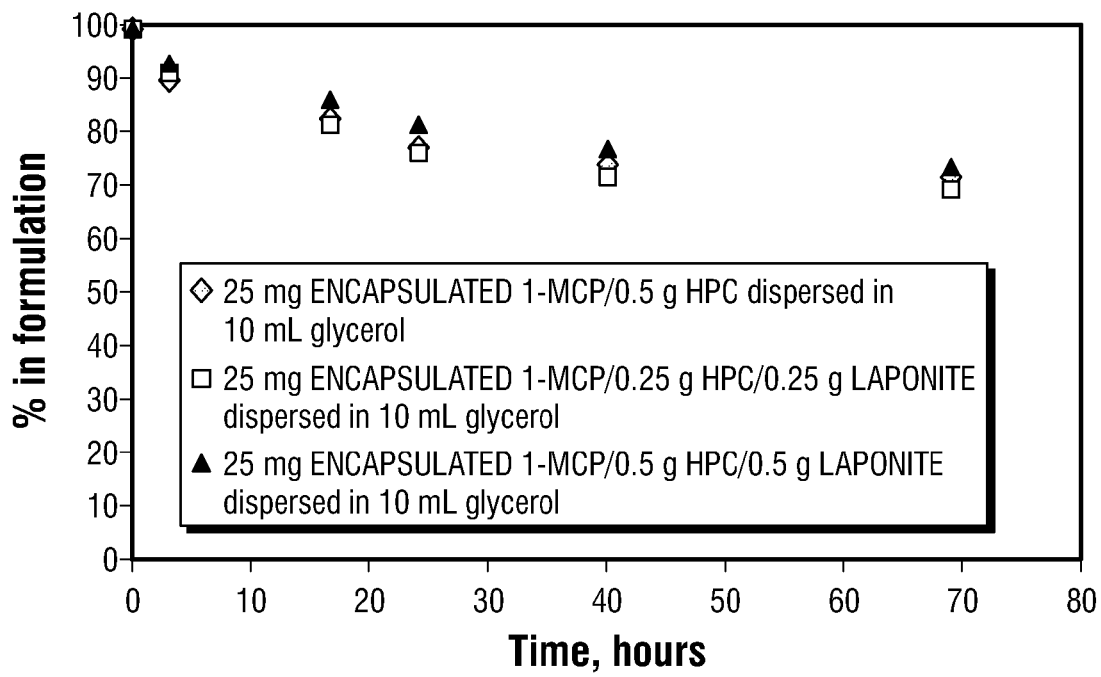
FIG. 9 shows the retention of encapsulated 1-MCP from the glycerol/hydrocolloid or glycerol/hydrocolloid/clay system at room temperature. Plotted from Data of Table 9.
Figure 10:
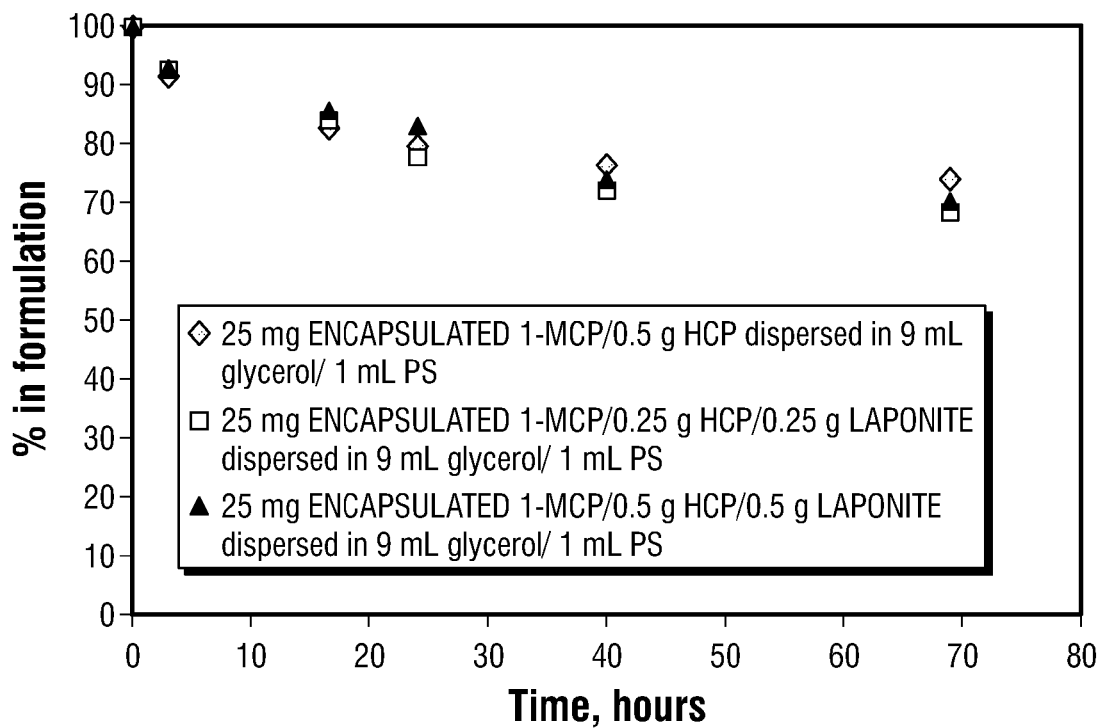
FIG. 10 shows the retention of encapsulated 1-MCP from the glycerol/polysorbate/hydrocolloid or glycerol/polysorbate/hydrocolloid/clay system at room temperature. Plotted from Data of Table 10.
Figure 11:
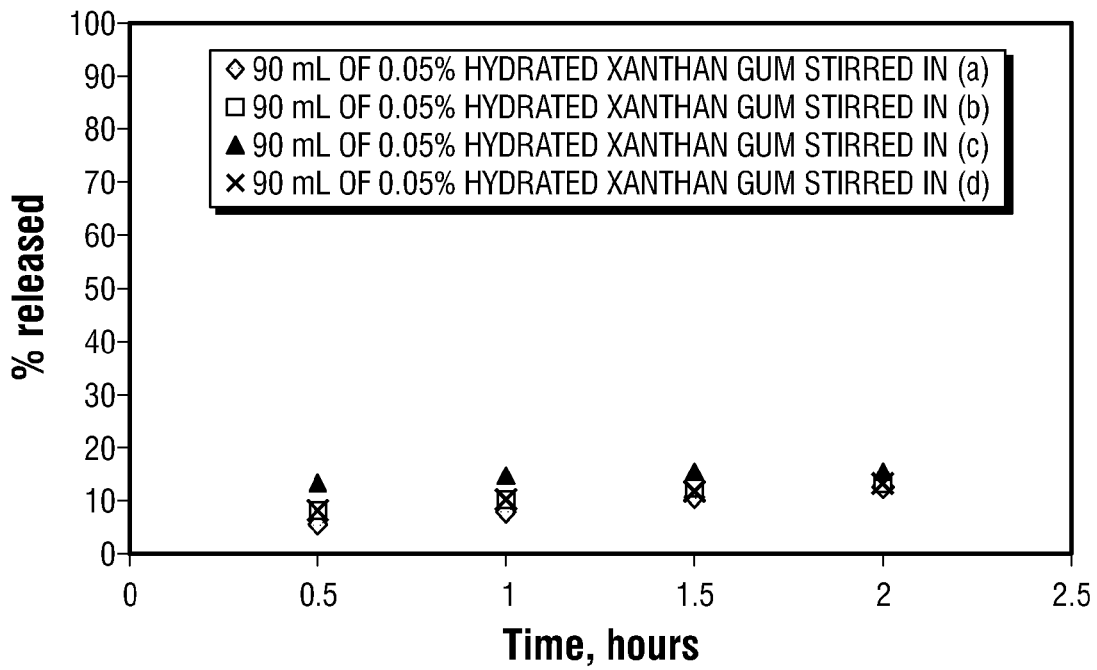
FIG. 11 shows the release of 1-MCP gas from the four formulations (a); (b); (c); (d) when mixed with hydrated 0.05% Xanthan gum. Plotted from Data of Table 11.
Figure 12:
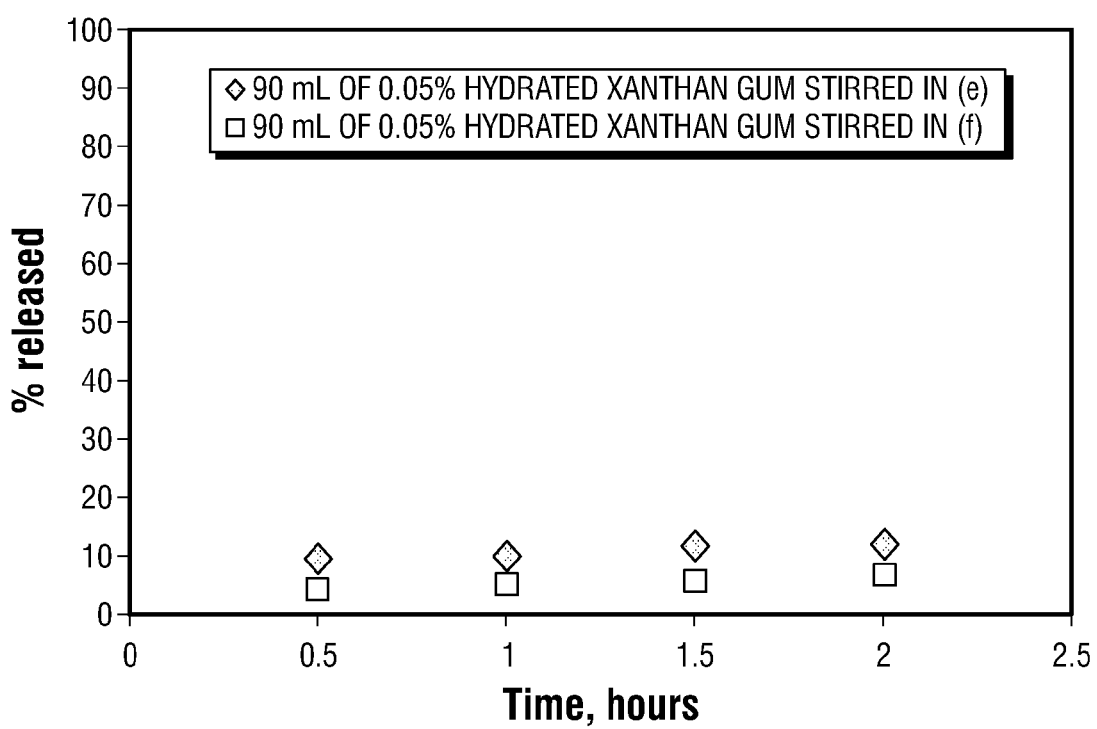
FIG. 12 shows the release of 1-MCP gas from formulations (e); (f) when mixed with hydrated 0.05% Xanthan gum. Plotted from Data of Table 12.
Figure 13:
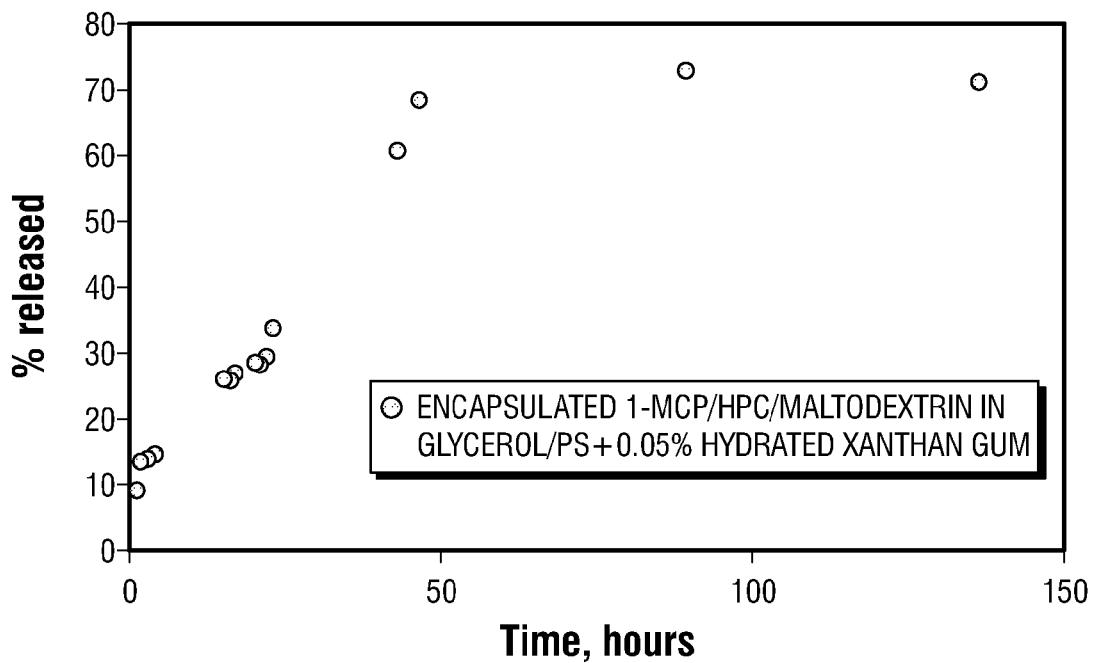
FIG. 13 shows the release profile of 1-MCP gas from polyol blend system when mixed with hydrated 0.05% Xanthan gum. Plotted from Data of Table 13.
Figure 14:
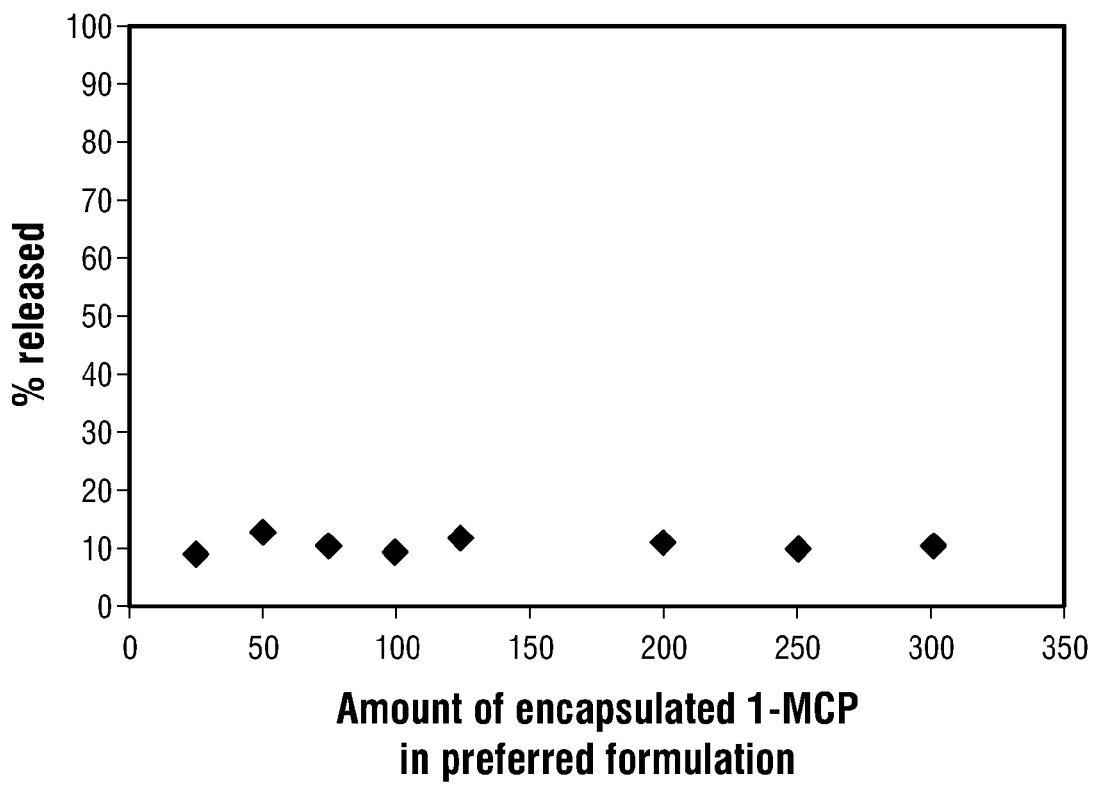
FIG. 14 shows the effect of various encapsulated 1-MCP loading levels on the release profile of 1-MCP gas from the invention. Plotted from Data of Table 14.

Table 6 and FIG. 6 show the effect of decreasing the droplet size of the solution by spraying under pressure vs. not spraying or stagnant on the release of encapsulated 1-MCP from the formulation. In both cases of using glycerol or sorbitol, spraying causes about 3 to 4 times increase in release of encapsulated 1-MCP compared to stagnant in about 60 min, which is still less than 21% compared to 100% release with water (Table 3; table 4; 0% XG).

TABLE 7

Effect of dispersing encapsulated 1-MCP hydrated Xanthan gum or hydrated Xanthan gum/hydroxyethyl cellulose on its release

| encapsulated 1-MCP + Xanthan gum (0.05%) dispersed in water | | | encapsulated 1-MCP + HEC (1%) dispersed in water + Xanthan gum (0.05%) dispersed in water | | |
|---|---|---|---|---|---|
| *100% release of 1-MCP from formulation: 1.45 ppm | | | | | |
| Time (hr) | ppm | % released | Time (hr) | ppm | % released |
| 0 | 0.000 | 0.00 | 0 | 0.000 | 0.00 |
| 1 | 0.000 | 0.00 | 1 | 0.000 | 0.00 |
| 2 | 0.063 | 4.36 | 3 | 0.084 | 5.78 |
| 3 | 0.106 | 7.33 | 4 | 0.153 | 10.56 |
| 5 | 0.206 | 14.19 | 5 | 0.216 | 14.87 |
| 7 | 0.257 | 17.74 | 7 | 0.311 | 21.47 |
| 8 | 0.294 | 20.30 | 8 | 0.444 | 30.62 |

Table 7 demonstrates the effect of hydrated xanthan gum or hydrated xanthan gum in combination with hydrated hydroxyethyl cellulose in controlling the release of encapsulated 1-MCP. In both cases the data shows 20-30% release of 1-MCP in 8 hours. Hydrated xanthan gum, by itself, seems more effective in slowing the release of encapsulated 1-MCP to about 20% in 8 hours compared to its combination with hydroxyethyl cellulose, where the release is around 30% in 8 hours.

TABLE 8

Percentage 1-MCP release from encapsulated 1-MCP
dispersed in D-sorbitol mixed with 0.5% hydrated carageenan gum
Sorbitol + encapsulated 1-MCP +
carageenan gum (0.5%) dispersed in water
*100% release of 1-MCP from formulation: 1.45 ppm

| Time (hr) | ppm | % released |
|---|---|---|
| 0 | 0.000 | 0.00 |
| 0.5 | 0.058 | 3.98 |

TABLE 8-continued

Percentage 1-MCP release from encapsulated 1-MCP
dispersed in D-sorbitol mixed with 0.5% hydrated carageenan gum
Sorbitol + encapsulated 1-MCP +
carageenan gum (0.5%) dispersed in water
*100% release of 1-MCP from formulation: 1.45 ppm

| Time (hr) | ppm | % released |
|---|---|---|
| 1 | 0.129 | 8.87 |
| 1.5 | 0.153 | 10.55 |
| 2 | 0.191 | 13.20 |
| 4 | 0.246 | 16.97 |
| 5 | 0.267 | 18.41 |
| 8 | 0.388 | 26.77 |

Table 8 shows that encapsulated 1-MCP dispersed in sorbitol when mixed with other hydrocolloid such as carageenan gum (0.5%) dispersed in water also helps in controlling the release of 1-MCP. The table shows about 26.77% of 1-MCP released in 8 hours, compared to 100% release with water in 1 hour (Table 3; table 4; 0% XG).

TABLE 9

Retention of encapsulated 1-MCP from the glycerol/hydrocolloid or glycerol/hydrocolloid/clay system at room temperature

| Time hr | encapsulated 1-MCP/HPC dispersed in glycerol | | encapsulated 1-MCP/HPC/ Laponite dispersed in glycerol | | encapsulated 1-MCP/HPC/ Laponite dispersed in glycerol | |
|---|---|---|---|---|---|---|
| | Ppm | % in the formulation | ppm | % in the formulation | ppm | % in the formulation |
| 0 | 3.33 | 99.61 | 0.84 | 99.90 | 2.74 | 99.68 |
| 3 | 78.86 | 90.73 | 68.15 | 91.99 | 55.62 | 93.46 |
| 16.5 | 145.84 | 82.86 | 153.77 | 81.92 | 116.27 | 86.33 |
| 24 | 191.90 | 77.44 | 197.28 | 76.81 | 154.10 | 81.89 |
| 40 | 220.06 | 74.13 | 236.73 | 72.17 | 192.46 | 77.38 |
| 69 | 237.44 | 72.09 | 259.76 | 69.46 | 222.91 | 73.80 |

Table 9 shows that 1-MCP gas released at room temperature, is only ≤31% (69% of 1-MCP left in the formulation) in a period of 69 hours, when a concentrated blend of glycerol/HPC (hydrocolloid) or glycerol/HPC/Laponite (clay) system containing encapsulated 1-MCP is left as such without the addition of water or a hydrated hydrocolloid.

TABLE 10

Retention of encapsulated 1-MCP from the glycerol/polysorbate/hydrocolloid or glycerol/polysorbate/hydrocolloid/clay system at room temperature

| Time hr | encapsulated 1-MCP/HPC dispersed in glycerol/PS | | encapsulated 1-MCP/HPC/0.25 g Laponite dispersed in glycerol/PS | | encapsulated 1-MCP/HPC/ Laponite dispersed in glycerol/PS | |
|---|---|---|---|---|---|---|
| | Ppm | % in the formulation | ppm | % in the formulation | ppm | % in the formulation |
| 0 | 2.59 | 99.70 | 0.76 | 99.91 | 0.90 | 99.89 |
| 3 | 60.84 | 92.85 | 56.78 | 93.33 | 55.05 | 93.53 |
| 16.5 | 143.02 | 83.19 | 130.25 | 84.69 | 117.99 | 86.13 |
| 24 | 165.29 | 80.57 | 184.56 | 78.30 | 134.81 | 84.15 |
| 40 | 195.80 | 76.98 | 230.19 | 72.94 | 213.17 | 74.94 |
| 69 | 216.63 | 74.54 | 263.22 | 69.06 | 252.62 | 70.30 |

Figure 3:
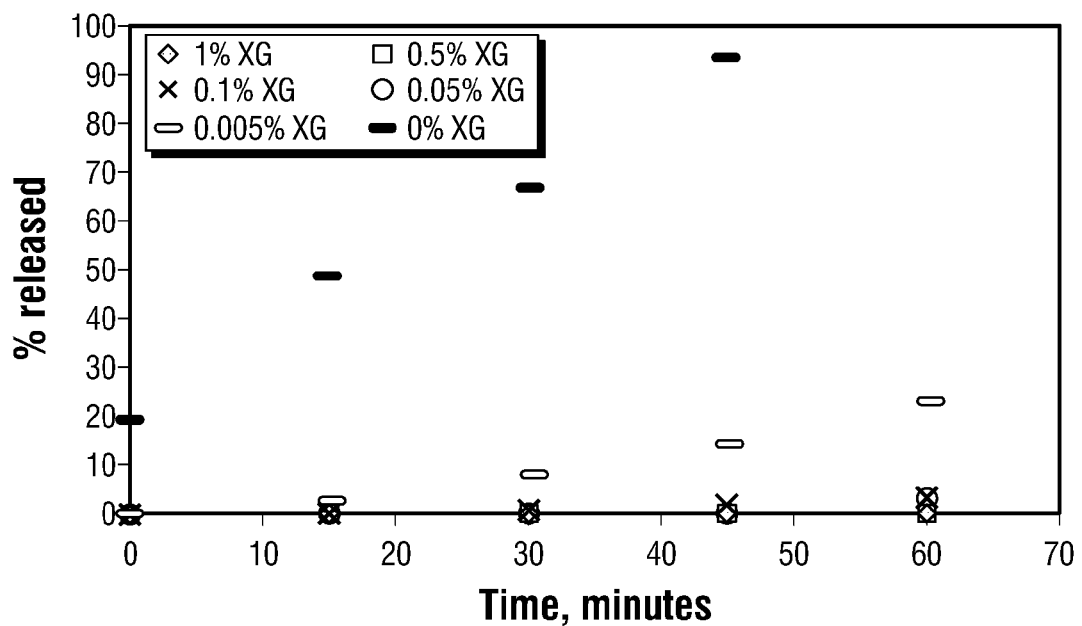
FIG. 3 shows the effect of varying Xanthan gum concentration on the release of 1-MCP gas from encapsulated 1-MCP dispersed in D-sorbitol (70%). Plotted from Data of Table 3.
Figure 4:
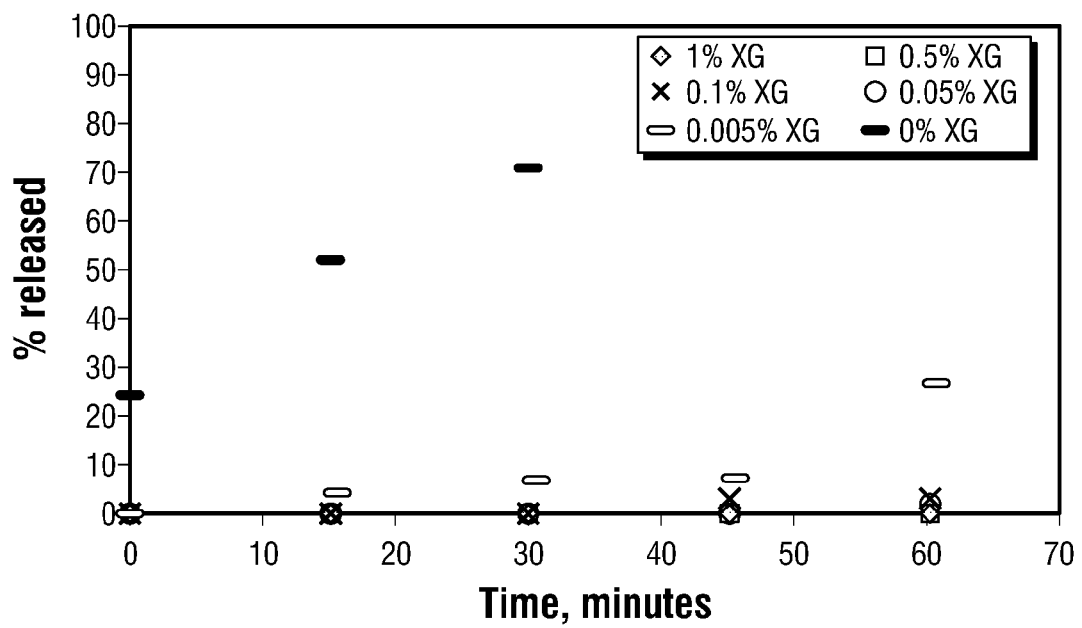
FIG. 4 shows the effect of varying Xanthan gum concentration on the release of 1-MCP gas from encapsulated 1-MCP dispersed in Glycerol (99.9%). Plotted from Data of Table 4.

Table 10 shows the effect of adding an emulsifier such as polysorbate to the concentrated blend of glycerol/HPC (hydrocolloid) or glycerol/HPC/Laponite (clay) system containing encapsulated 1-MCP and left as such without the addition of water or a hydrated hydrocolloid. The resultant system shows that 1-MCP gas released at room temperature is only ≤31% (69% of 1-MCP left in the formulation) in a period of 69 hours. By comparison, comparative formulation comprising of water plus encapsulated 1-MCP does not retain 1-MCP beyond 1 hour of holding (see table 3 and FIG. 3).

TABLE 11

Release of 1-MCP gas from the four formulations (a); (b); (c); (d) when mixed with hydrated 0.05% Xanthan gum 0.05% hydrated Xanthan gum stirred in (a); (b); (c) and (d)

| Time | (a) encapsulated 1-MCP/ HPC dispersed in glycerol/PS | | (b) encapsulated 1-MCP/HPC/ Laponite dispersed in glycerol/ 1 mL PS | | (c) encapsulated 1-MCP/HPC/ Laponite dispersed in glycerol/PS | | (d) encapsulated 1-MCP/HPC/ Laponite/TSPP dispersed in glycerol/PS | |
|---|---|---|---|---|---|---|---|---|
| hr | ppm | *% released | ppm | *% released | ppm | *% released | ppm | *% released |
| 0.5 | 0.09 | 6.31 | 0.12 | 8.09 | 0.19 | 13.28 | 0.13 | 9.17 |
| 1 | 0.12 | 8.25 | 0.15 | 10.61 | 0.21 | 14.71 | 0.15 | 10.57 |
| 1.5 | 0.16 | 10.97 | 0.19 | 12.89 | 0.23 | 15.85 | 0.17 | 11.80 |
| 2 | 0.19 | 13.19 | 0.20 | 13.91 | 0.23 | 15.68 | 0.19 | 12.91 |

Table 11 demonstrates that 1-MCP release is controlled to about 13-16% in 2 hours when the encapsulated 1-MCP is blended to formulations (a); (b); (c) and (d) and hydrated Xanthan gum solution is added to the blend.

TABLE 12

Release of 1-MCP gas from formulations (e); (f) when mixed with hydrated 0.05% Xanthan gum

| | 0.05% hydrated Xanthan gum stirred in (e)and (f) | | | |
|---|---|---|---|---|
| | (e) encapsulated 1-MCP/ HPC/Maltodextrin dispersed in glycerol/PS | | (f) encapsulated 1-MCP/HPC/ Laponite/Maltodextrin dispersed in glycerol/PS | |
| Time | | | | |
| hr | Ppm | % released | ppm | % released |
| 0.5 | 0.13 | 9.09 | 0.06 | 4.47 |
| 1 | 0.14 | 9.74 | 0.08 | 5.25 |
| 1.5 | 0.16 | 11.20 | 0.09 | 6.05 |
| 2 | 0.17 | 12.00 | 0.10 | 6.70 |

Table 12 shows that the addition of maltodextrin to formulations (e) and (f) regulates the release of 1-MCP to about 12% in formulation (e) and to about 6.7% in formulation (f), when stirred with hydrated Xanthan gum solution.

TABLE 13

Release profile of 1-MCP gas from polyol blend system when mixed with hydrated 0.05% Xanthan gum encapsulated 1-MCP/HPC/Maltodextrin in glycerol/PS mixed with 0.05% hydrated Xanthan gum

| time, hr | ppm | *% released |
|---|---|---|
| 1 | 0.118886 | 9.700 |
| 2 | 0.168817 | 13.775 |
| 3 | 0.172454 | 14.071 |
| 4 | 0.181956 | 14.847 |
| 15 | 0.323141 | 26.366 |
| 16 | 0.319817 | 26.095 |
| 17 | 0.334142 | 27.264 |
| 20 | 0.351606 | 28.689 |
| 21 | 0.349041 | 28.480 |
| 22 | 0.366497 | 29.904 |
| 23 | 0.418878 | 34.178 |
| 43 | 0.745569 | 60.834 |
| 46.5 | 0.840453 | 68.576 |
| 89 | 0.894203 | 71.344 |
| 136 | 0.874369 | 72.962 |

Table 13 demonstrates that about 73% 1-MCP is released in 5.6 days, when encapsulated 1-MCP is dispersed in polyol blend system (glycerol/polysorbate/HPC/maltodextrin) and mixed with hydrated Xanthan gum solution.

TABLE 14

Effect of various encapsulated 1-MCP loading levels on the release profile of 1-MCP gas from the invention encapsulated 1-MCP/HPC/Maltodextrin dispesed in glycerol/PS

| Amount of encapsulated 1-MCP (mg) | % released in 3 hours |
|---|---|
| 25 | 9.01 |
| 50 | 12.56 |
| 75 | 10.47 |
| 100 | 9.04 |
| 125 | 11.75 |
| 200 | 10.65 |
| 250 | 9.57 |
| 300 | 10.20 |

Table 14 shows that varying amounts of 1-MCP from 25 mg to 300 mg in polyol blend system (glycerol/polysorbate/HPC/maltodextrin), does not dramatically change the percentage of 1-MCP lost from the formulation. In all cases, the release seems to vary between 9 to 13% in 3 hours. This clearly demonstrates the suitability of the invention for a wide range of active compound holding and subsequent controlled or slow release for application.

The invention claimed is:

1. An in-situ method of reducing loss of 1-methylcyclopropene (1-MCP) in a modifying plant ethylene response formulation to be applied to at least one target plant in a direct soil application comprising the steps of:
    a) mixing or suspending 1-methylcyclopropene (1-MCP) at least partially encapsulated with at least one encapsulant, in a water based medium, to form a 1-MCP control release mixture comprising encapsulated 1-MCP and free 1-MCP,
    b) forming a 1-MCP control release liquid formulation from the mixture in a continuous stirred tank system, and
    c) immediately spraying the 1-MCP control release formulation, within or less than 1 hour of formulation formation, onto at the least one target plant in a direct soil application, wherein less than 80% by weight gaseous or volatile 1-MCP is released into a headspace of an airtight chamber from the 1-MCP controlled release liquid formulation.

2. The method of claim 1 wherein the formulation comprises from about 0.01 to about 10,000 milligrams by weight of said 1-MCP per liter.

3. The method of claim 1 wherein the formulation is applied at a rate of from about 0.1 gram to about 100 grams of said 1-MCP per hour.

4. The method of claim 1 wherein the encapsulant is cyclodextrin.

5. The method of claim 1 wherein the encapsulant is α-cyclodextrin or modified α-cyclodextrin.

6. The method of claim 1 wherein the encapsulant is β-cyclodextrin or modified β-cyclodextrin.

7. The method of claim 1 wherein the encapsulant is γ-cyclodextrin or modified γ-cyclodextrin.

8. The method of claim 1 wherein a ratio of encapsulated to non-encapsulated 1-MCP can be about 99:1 to about 50:50.

9. The method of claim 1 wherein the formulation further comprises at least one pesticide.

10. The method of claim 9 wherein the pesticide is selected from the group consisting of fungicide, insecticide and biopesticide.

11. The method of claim 1 wherein the formulation further comprises at least one plant growth regulator.

12. The method of claim 11 wherein the plant growth regulator is selected from the group consisting of gibberellic acid, etheral and aminoethoxyvinylglycine.

13. The method of claim 1 wherein the formulation further comprises a surfactant.

14. The method of claim 13 wherein the surfactant is selected from the group consisting of anionic, cationic, nonionic, zwitterionic and ampholytic surfactants.

15. An in-situ method of reducing loss of 1-methylcyclopropene (1-MCP) in a modifying plant ethylene response formulation to be applied to at least one target plant in a direct soil application using an automated combination mixing and spraying equipment comprising the steps of:
    a) mixing or suspending 1-methylcyclopropene (1-MCP), at least partially encapsulated with at least one encapsulant, in a water based medium, to form a 1-MCP control release mixture comprising encapsulated 1-MCP and free 1-MCP, b) passing the mixture into a stirred tank system to form a 1-MCP controlled release liquid formulation, and c) immediately spraying the volatile 1-MCP control release liquid formulation onto at least one target plant in a direct soil application within or less than 1 hour of formulation formation such that the formulation remains sprayable and wherein less than 80% by weight gaseous or volatile 1-MCP is released into a headspace of an airtight chamber from the 1-MCP controlled release liquid formulation.

16. The method of claim 15 wherein the encapsulant is cyclodextrin.

17. The method of claim 15 wherein the encapsulant is α-cyclodextrin or modified α-cyclodextrin.

18. The method of claim 15 wherein the encapsulant is β-cyclodextrin or modified β-cyclodextrin.

19. The method of claim 15 wherein the encapsulant is γ-cyclodextrin or modified γ-cyclodextrin.

20. The method of claim 15 wherein the formulation further comprises a surfactant.

21. The method of claim 20 wherein the surfactant is selected from the group consisting of anionic, cationic, non-ionic, zwitterionic and ampholytic surfactants.

22. An in-situ method of reducing loss of 1-methylcyclopropene (1-MCP) in a modifying plant ethylene response formulation to be applied to at least one target plant in a direct soil application comprising the steps of:

a) mixing or suspending 1-methylcyclopropene (1-MCP) powder encapsulated with at least one encapsulant, in a water based medium, to form a volatile 1-MCP control release liquid formulation comprising encapsulated 1-MCP and free 1-MCP, and b) spraying the volatile 1-MCP control release liquid formulation onto at least one target plant in a direct soil application within or less than 1 hour of formulation formation such that the formulation remains sprayable and wherein less than 80% by weight gaseous or volatile 1-MCP is released into a headspace of an airtight chamber from the 1-MCP controlled release liquid formulation.

23. The method of claim 22 wherein the formulation further comprises at least one antimicrobial.

24. The method of claim 23 wherein the antimicrobial is selected from the group consisting of chlorine dioxide, sulphur dioxide, thymol, carvacrol, cinnamaldehyde, allyl isothiocyanate, ethanol, oregano extracts, other synthetic or natural occurring flavanols, phenolic compounds and organic acids.

25. The method of claim 22 wherein the formulation further comprises at least one antioxidant.

26. The method of claim 25 wherein the antioxidant is diphenyl amine or ethoxyquin.

27. The method of claim 22 wherein the formulation further comprises at least one plant growth regulator.

28. The method of claim 27 wherein the plant growth regulator is selected from the group consisting of gibberellic acid, etheral and aminoethoxyvinylglycine.

29. The method of claim 22 wherein the formulation further comprises a surfactant.

30. The method of claim 29 wherein the surfactant is selected from the group consisting of anionic, cationic, non-ionic, zwitterionic and ampholytic surfactants.

* * * * *